US 9,993,587 B2

(12) United States Patent
Farnan et al.

(10) Patent No.: US 9,993,587 B2
(45) Date of Patent: Jun. 12, 2018

(54) INFLOW CANNULA TUNNELING TOOL ALLOWING QUICK EXCHANGE WITH DILATING PLUG

(71) Applicant: CircuLite, Inc., Teaneck, NJ (US)

(72) Inventors: Robert C. Farnan, Fort Lauderdale, FL (US); Brad Aurilia, Coconut Creek, FL (US); Cesar Gomez, Homestead, FL (US)

(73) Assignee: CircuLite, Inc., Teaneck, NJ (US)

( * ) Notice: Subject to any disclaimer, the term of this patent is extended or adjusted under 35 U.S.C. 154(b) by 0 days. days.

(21) Appl. No.: 14/706,226

(22) Filed: May 7, 2015

(65) Prior Publication Data

US 2016/0325032 A1 Nov. 10, 2016

(51) Int. Cl.
*A61M 1/10* (2006.01)
*A61M 1/36* (2006.01)
(Continued)

(52) U.S. Cl.
CPC ....... *A61M 1/1008* (2014.02); *A61B 17/0401* (2013.01); *A61B 17/3415* (2013.01);
(Continued)

(58) Field of Classification Search
CPC ...... A61M 1/10; A61M 1/1008; A61M 1/122; A61M 1/3659; A61B 17/0401; A61B 17/3415
(Continued)

(56) References Cited

U.S. PATENT DOCUMENTS

| 4,445,896 A | 5/1984 | Gianturco |
| 5,766,151 A * | 6/1998 | Valley ............ A61B 17/00234 604/103.07 |

(Continued)

FOREIGN PATENT DOCUMENTS

| EP | 1993640 A2 | 11/2008 |
| WO | 2011059908 A1 | 5/2011 |

(Continued)

OTHER PUBLICATIONS

U.S. Patent and Trademark Office, Office Action in U.S. Appl. No. 14/313,270, dated May 19, 2016.
(Continued)

*Primary Examiner* — Christopher A Flory
(74) *Attorney, Agent, or Firm* — Christopher & Weisberg, P.A.

(57) ABSTRACT

A system for facilitating fluid connection between cannulae and a blood pump. The system includes a cannula having a distal end adapted to be in fluid communication with the circulatory system and a proximal end configured to couple to an inlet of the blood pump. Further included is a tunneling device configured to be inserted into a body of a patient to direct the proximal end of the cannula adjacent to the inlet and including a second connecting structure. Further included is a plug which has a first plug part and a second plug part. The first plug part includes a second connecting structure, the first and second connecting structures being selectively engageable. The second plug part is configured to be inserted in the proximal end of the cannula. The first and second plug parts are selectively disengageable to allow in situ disconnection between the cannula and tunneling device.

10 Claims, 22 Drawing Sheets

(51) Int. Cl.
  *A61B 17/04* (2006.01)
  *A61B 17/34* (2006.01)
  *A61M 1/12* (2006.01)
  *A61B 17/32* (2006.01)
  *A61M 25/01* (2006.01)

(52) U.S. Cl.
  CPC .................. *A61M 1/3659* (2014.02); *A61B 2017/320056* (2013.01); *A61M 1/101* (2013.01); *A61M 1/122* (2014.02); *A61M 25/0194* (2013.01)

(58) Field of Classification Search
  USPC .......................................................... 600/16
  See application file for complete search history.

(56) References Cited

U.S. PATENT DOCUMENTS

| | | | | |
|---|---|---|---|---|
| 5,814,016 | A * | 9/1998 | Valley | A61B 17/00234 604/96.01 |
| 5,863,366 | A * | 1/1999 | Snow | A61B 17/12022 156/143 |
| 6,210,397 | B1 * | 4/2001 | Aboul-Hosn | A61B 17/3423 604/164.11 |
| 6,245,007 | B1 * | 6/2001 | Bedingham | A61M 1/101 600/16 |
| 6,251,093 | B1 * | 6/2001 | Valley | A61B 17/12022 604/97.03 |
| 6,482,171 | B1 * | 11/2002 | Corvi | A61M 25/0133 156/175 |
| 6,533,770 | B1 * | 3/2003 | Lepulu | A61M 25/0012 604/264 |
| 6,969,379 | B1 * | 11/2005 | Aboul-Hosn | A61M 25/0043 128/898 |
| 8,088,138 | B2 | 1/2012 | Pandey | |
| 8,157,720 | B2 | 4/2012 | Marseille et al. | |
| 8,333,727 | B2 * | 12/2012 | Farnan | A61M 1/3655 600/16 |
| 8,545,379 | B2 | 10/2013 | Marseille et al. | |
| 8,768,487 | B2 | 7/2014 | Farnan et al. | |
| 8,939,882 | B2 * | 1/2015 | Reichenbach | A61M 1/3653 600/16 |
| 9,168,352 | B2 * | 10/2015 | Kelly | A61M 25/0026 |
| 2002/0099319 | A1 * | 7/2002 | Saito | A61M 1/3693 604/6.04 |
| 2005/0148997 | A1 * | 7/2005 | Valley | A61B 17/12022 604/509 |
| 2006/0235357 | A1 * | 10/2006 | Woodward | A61M 1/122 604/264 |
| 2006/0276681 | A1 | 12/2006 | Bolling | |
| 2007/0134993 | A1 * | 6/2007 | Tamez | A61M 1/10 439/752 |
| 2007/0173879 | A1 | 7/2007 | Pandey | |
| 2007/0185430 | A1 * | 8/2007 | Brugger | A61M 1/3462 604/6.09 |
| 2007/0197855 | A1 | 8/2007 | Richardson et al. | |
| 2007/0197856 | A1 | 8/2007 | Gellman et al. | |
| 2008/0076959 | A1 * | 3/2008 | Farnan | A61M 1/12 600/16 |
| 2009/0023975 | A1 | 1/2009 | Marseille et al. | |
| 2009/0082778 | A1 * | 3/2009 | Beane | A61B 17/11 606/108 |
| 2009/0149950 | A1 * | 6/2009 | Wampler | A61M 1/101 623/3.13 |
| 2009/0182188 | A1 | 7/2009 | Marseille et al. | |
| 2009/0203957 | A1 | 8/2009 | LaRose et al. | |
| 2009/0270809 | A1 | 10/2009 | Duenas | |
| 2010/0249490 | A1 * | 9/2010 | Farnan | A61M 1/101 600/16 |
| 2010/0298625 | A1 * | 11/2010 | Reichenbach | A61M 1/3653 600/16 |
| 2011/0066170 | A1 | 3/2011 | Farnan | |
| 2011/0087063 | A1 * | 4/2011 | Farnan | A61M 1/3655 600/16 |
| 2011/0112353 | A1 * | 5/2011 | Farnan | A61M 1/10 600/16 |
| 2011/0118668 | A1 * | 5/2011 | Farnan | A61M 25/04 604/164.01 |
| 2011/0137234 | A1 * | 6/2011 | Farnan | A61M 1/12 604/22 |
| 2011/0213316 | A1 * | 9/2011 | Ibrahim | A61M 1/3653 604/264 |
| 2012/0059212 | A1 * | 3/2012 | LaRose | A61M 1/12 600/16 |
| 2012/0220815 | A1 * | 8/2012 | Richardson | A61M 1/3653 600/16 |
| 2012/0296152 | A1 * | 11/2012 | Reichenbach | A61M 1/3653 600/16 |
| 2013/0060267 | A1 * | 3/2013 | Farnan | A61B 17/11 606/153 |
| 2013/0158338 | A1 * | 6/2013 | Kelly | A61M 25/0026 600/16 |
| 2013/0172661 | A1 | 7/2013 | Farnan et al. | |
| 2013/0231521 | A1 * | 9/2013 | Farnan | A61M 1/101 600/16 |
| 2013/0245361 | A1 * | 9/2013 | Wampler | A61M 1/101 600/16 |
| 2014/0005467 | A1 * | 1/2014 | Farnan | A61M 1/101 600/16 |
| 2014/0073837 | A1 * | 3/2014 | Kerkhoffs | A61M 1/1086 600/16 |
| 2014/0100430 | A1 * | 4/2014 | Beane | A61B 17/11 600/207 |
| 2014/0200550 | A1 * | 7/2014 | Farnan | A61M 1/3653 604/509 |
| 2014/0249357 | A1 * | 9/2014 | Farnan | A61M 1/1008 600/16 |
| 2014/0257018 | A1 * | 9/2014 | Farnan | A61M 1/1008 600/16 |
| 2014/0275723 | A1 * | 9/2014 | Fritz, IV | A61M 1/1015 600/16 |
| 2014/0303427 | A1 * | 10/2014 | Kerkhoffs | A61M 1/1008 600/16 |
| 2014/0364880 | A1 * | 12/2014 | Farnan | A61B 17/11 606/151 |
| 2015/0005570 | A1 * | 1/2015 | Fritz | A61M 1/1008 600/16 |
| 2015/0224240 | A1 * | 8/2015 | Farnan | A61M 1/3653 600/16 |
| 2015/0250933 | A1 * | 9/2015 | Kerkhoffs | A61N 1/372 604/500 |
| 2015/0273124 | A1 * | 10/2015 | Callaway | A61M 1/12 623/3.26 |
| 2015/0335801 | A1 | 11/2015 | Farnan et al. | |
| 2015/0335804 | A1 * | 11/2015 | Marseille | A61M 1/1086 600/17 |
| 2016/0082176 | A1 * | 3/2016 | Kelly | A61M 25/0026 600/16 |

FOREIGN PATENT DOCUMENTS

| | | | |
|---|---|---|---|
| WO | 2013086408 | A2 | 6/2013 |
| WO | 2014062827 | A1 | 4/2014 |
| WO | 2014138146 | A2 | 9/2014 |
| WO | 2015013666 | A1 | 1/2015 |

OTHER PUBLICATIONS

European Patent Office, International Search Report and Written Opinion in PCT Application Serial No. PCT/US2014/044007, dated Oct. 15, 2014.
The International Bureau of WIPO, International Preliminary Report on Patentability in PCT Application Serial No. PCT/US2014/044007, dated Jan. 7, 2016.
U.S. Patent and Trademark Office, International Search Report and Written Opinion in PCT Application Serial No. PCT/US2016/029416, dated Aug. 25, 2016.
U.S. Patent and Trademark Office, Office Action in U.S. Appl. No. 14/924,842, dated Oct. 20, 2016.

(56) References Cited

OTHER PUBLICATIONS

European Patent Office, International Search Report and Written Opinion in PCT Application Serial No. PCT/US2015/059440, dated Jul. 20, 2016.

* cited by examiner

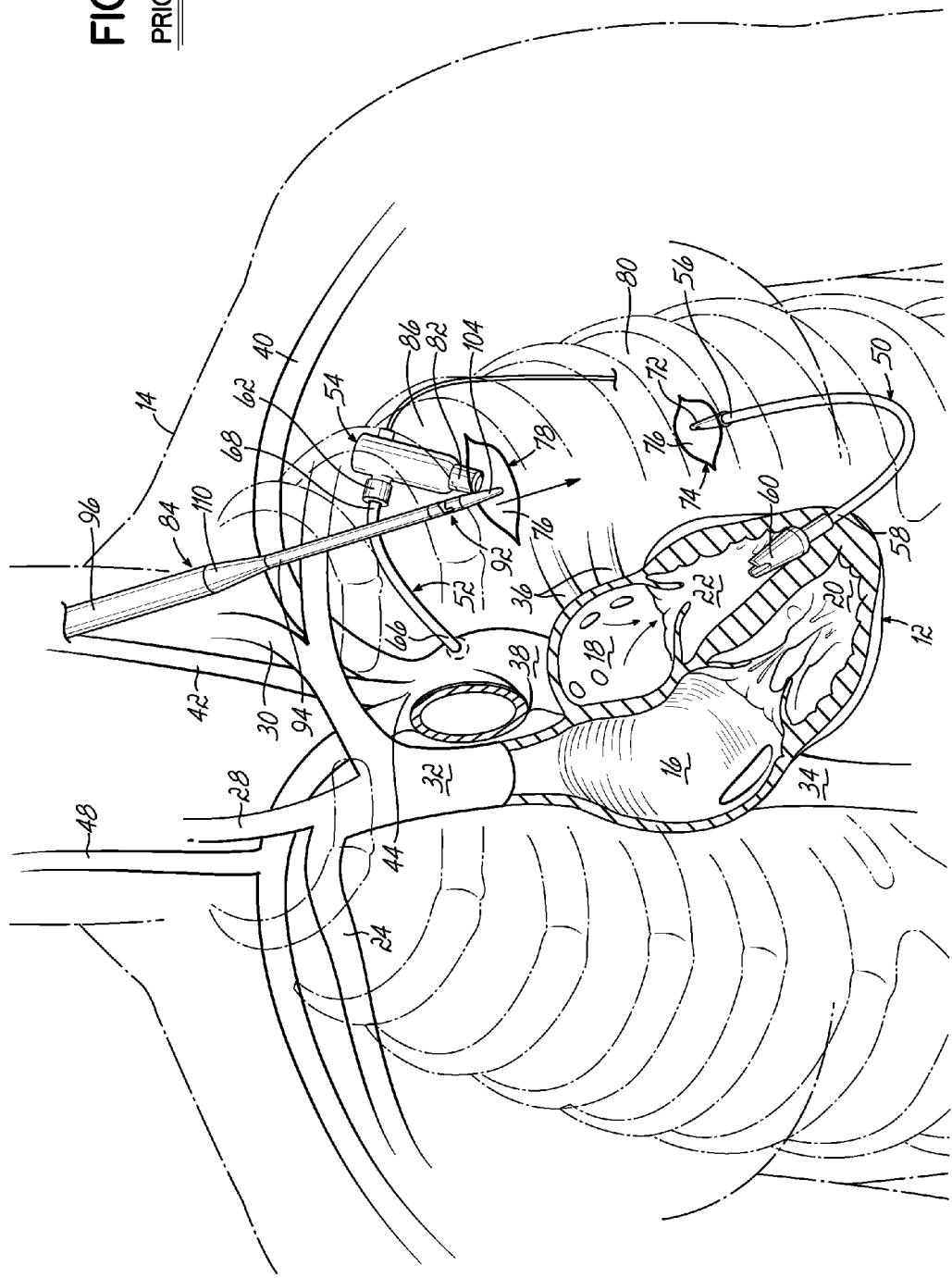

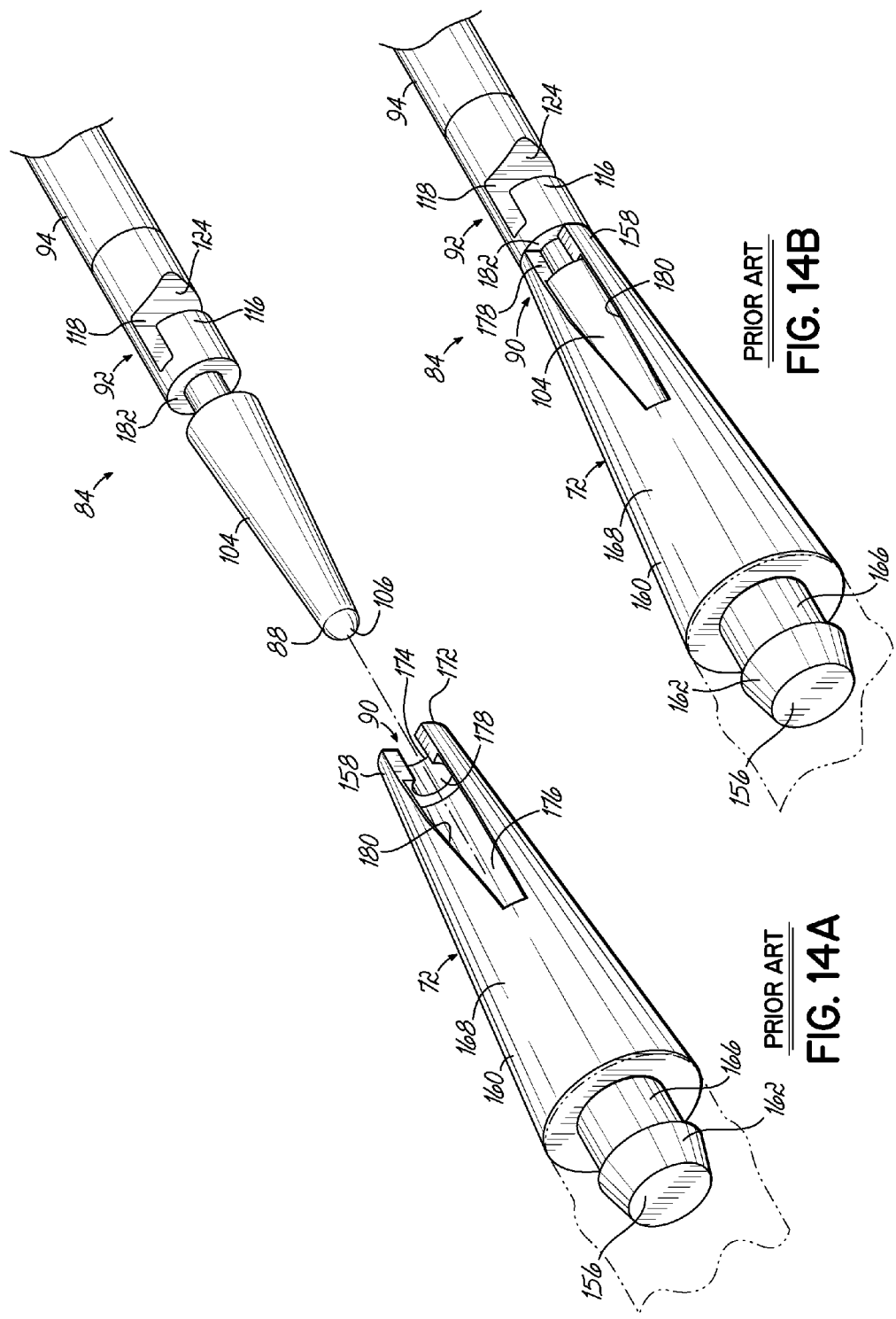

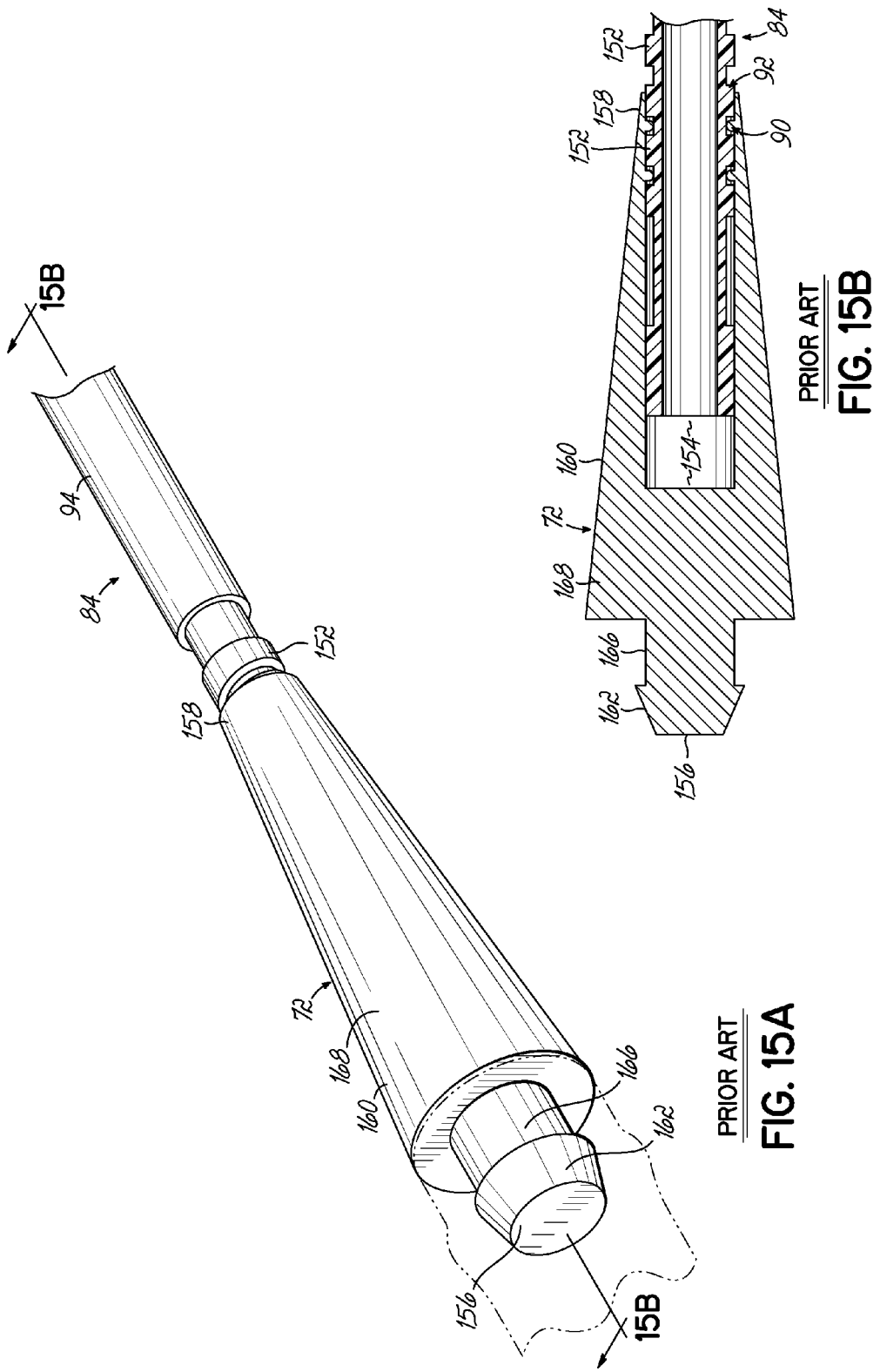

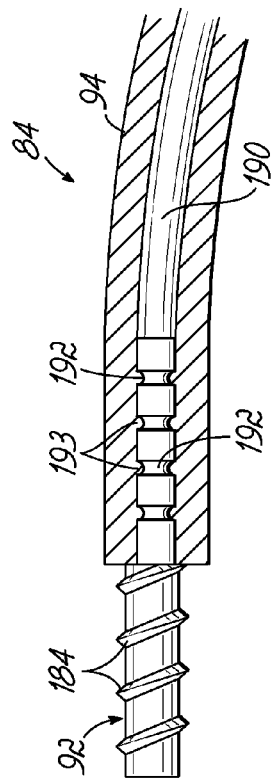
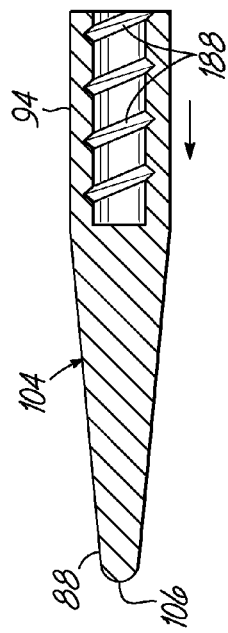
PRIOR ART
FIG. 16A
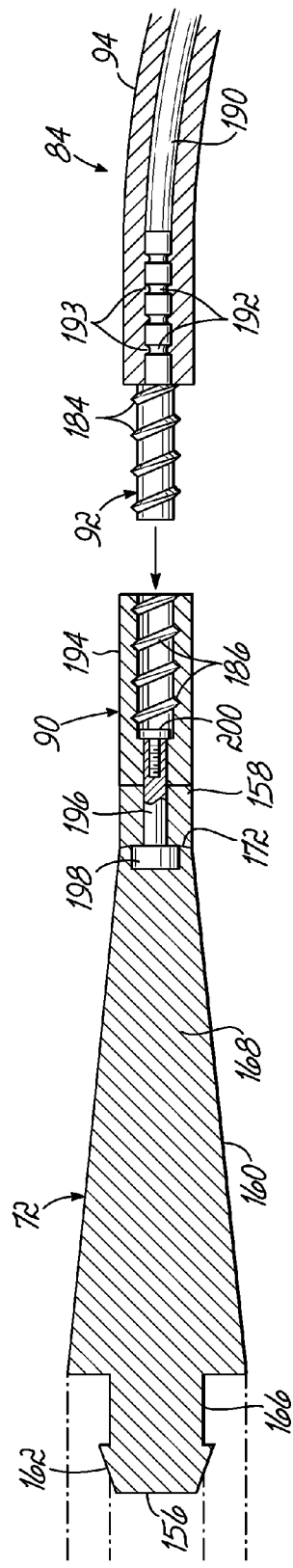
PRIOR ART
FIG. 16B

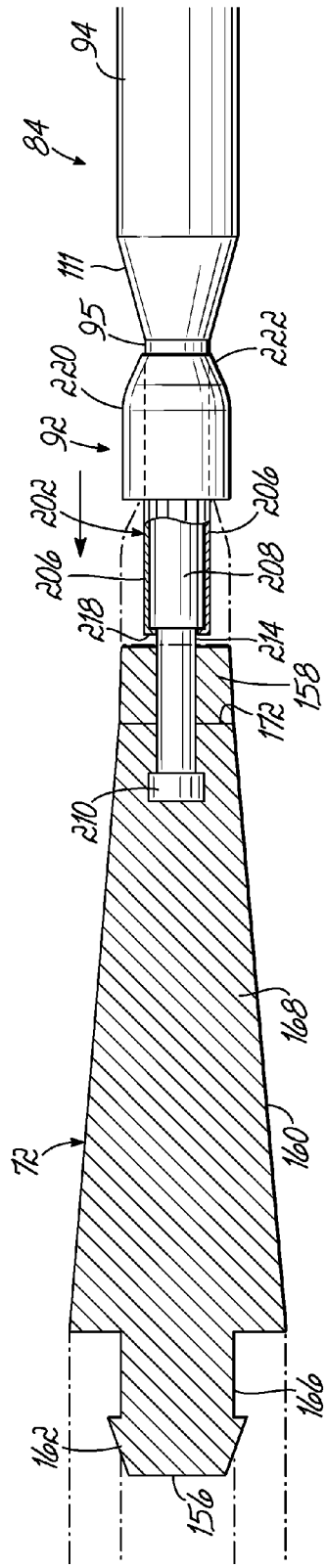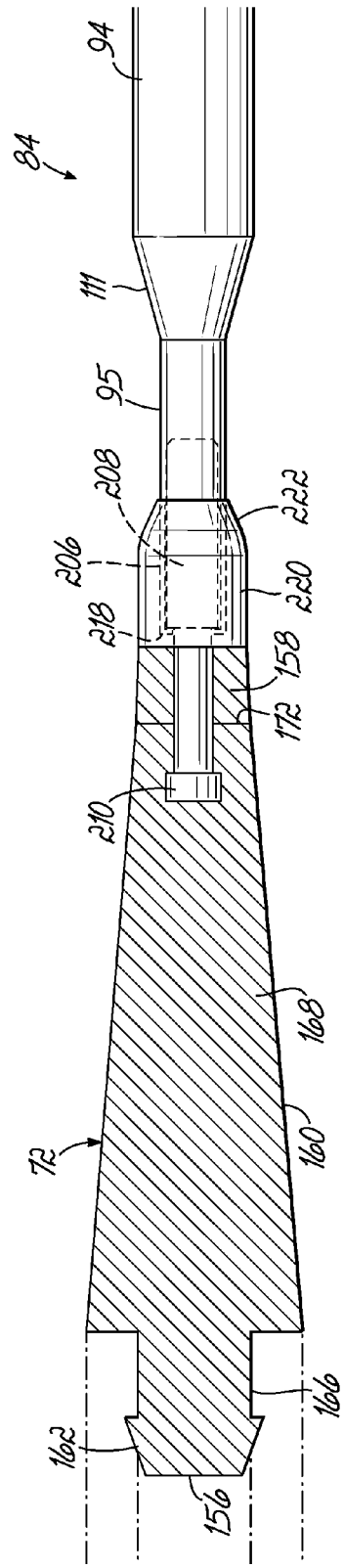
PRIOR ART
FIG. 17C
PRIOR ART
FIG. 17D

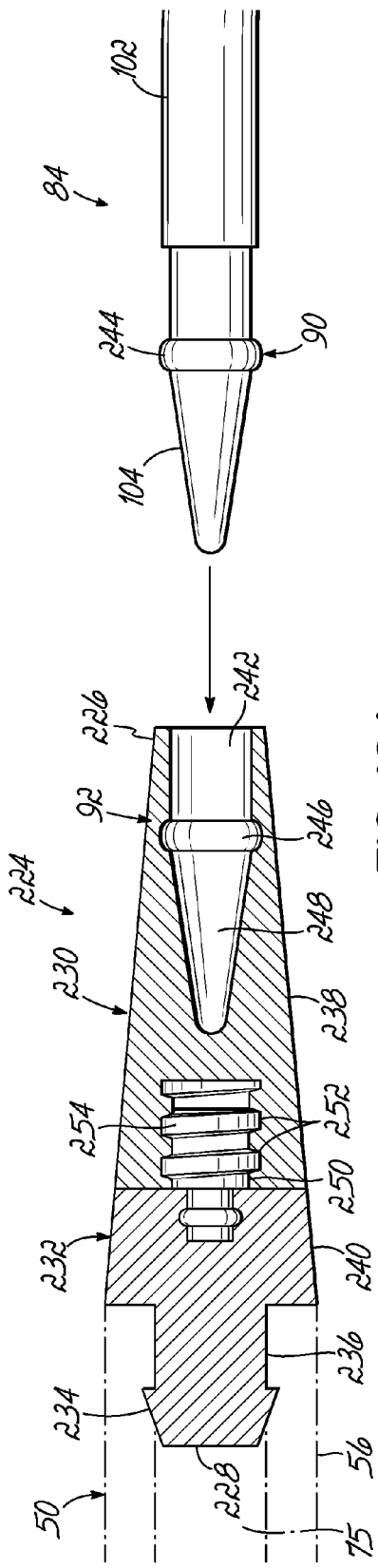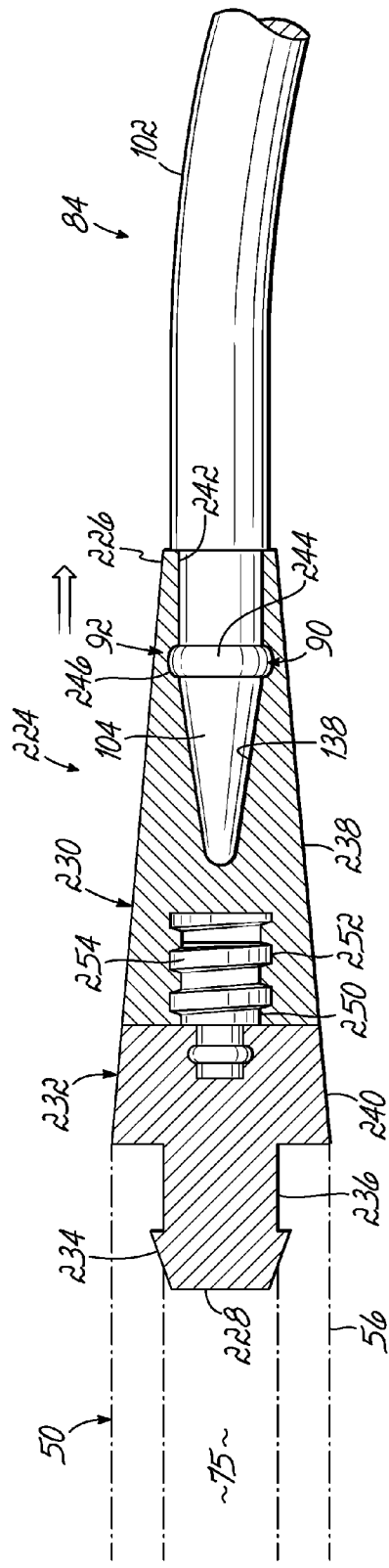
FIG. 18A
FIG. 18B

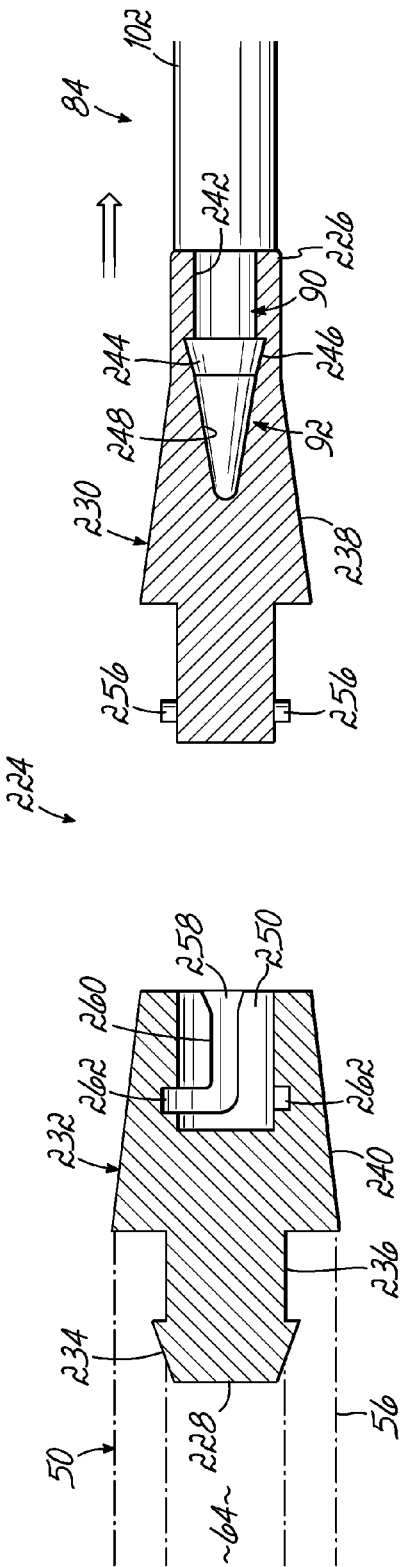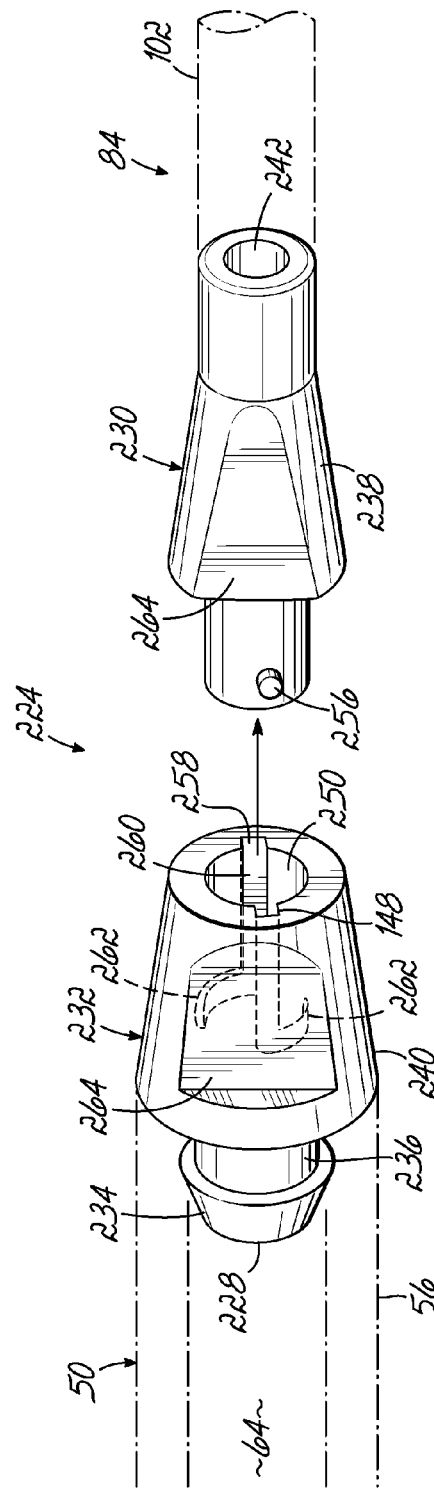
FIG. 19C
FIG. 20

INFLOW CANNULA TUNNELING TOOL ALLOWING QUICK EXCHANGE WITH DILATING PLUG

CROSS-REFERENCE TO RELATED APPLICATIONS

This application is related to U.S. patent application Ser. No. 14/313,270, filed Jun. 24, 2014 (pending), the disclosure of which is hereby incorporated by reference herein.

TECHNICAL FIELD

The invention generally relates to blood pumps and ancillary devices for connecting the blood pump to associated cannulae.

BACKGROUND

The human heart is the muscle that is responsible for pumping blood throughout the vascular network. Veins are vessels that carry blood toward the heart while arteries carry blood away from the heart. The human heart consists of two atrial chambers and two ventricular chambers. Atrial chambers receive blood from the body and the ventricular chambers, which include larger muscular walls, pump blood from the heart. A septum separates the left and the right sides of the heart. Movement of the blood is as follows: blood enters the right atrium from either the superior or inferior vena cava and moves into the right ventricle. From the right ventricle, blood is pumped to the lungs via pulmonary arteries to become oxygenated. Once the blood has been oxygenated, the blood returns to the heart by entering the left atrium, via the pulmonary veins, and into the left ventricle. Finally, the blood is pumped from the left ventricle into the aorta and the vascular network.

For the vast majority of the population, the events associated with the movement of blood happen without circumstance. However, for many people the heart fails to provide adequate pumping capabilities. These heart failures may include congestive heart failure (commonly referred to as heart disease), which is a condition that results in any structural or functional cardiac disorder that impairs the ability of the heart to fill with or pump blood throughout the body. Presently, there is no known cure for heart disease and long-term treatment is limited to a heart transplant. With only a little over 2,000 patients receiving a heart transplant each year, and over 16,600 more on the waiting list for a heart, there is a persisting need for a cure or at the minimum a means of improving the quality of life of those patients on the waiting list.

One such means of bridging the time gap while awaiting a transplant is a circulatory assist system. Circulatory assist systems may also be utilized as a destination therapy for individuals not eligible for a heart transplant. These systems, originally envisioned over thirty years ago, provide assistance to the heart by way of a mechanical pump. In this way, blood is circulated throughout the vascular network despite the diseased heart tissue. Traditionally, these circulatory assist systems include an implantable or extracorporeal pump, a controller (internal or external), and inflow and outflow tubes connecting the pump to the heart and the vascular network. Food and Drug Administration (FDA) approved circulatory assist systems can partially relieve symptoms of breathlessness and fatigue associated with severe heart failure and drastically improve quality of life.

Implantable pumps may reside in a "pump pocket," which is a subcutaneous or submuscular space on the chest of a patient, near the clavicle or shoulder. Once the inflow tube is connected to the heart, it normally resides within the thoracic cavity until connected with the pump. In order to access the chest cavity and reach the tube, practitioners must tunnel through the intercostal space adjacent the pump pocket. Once in the thoracic cavity, the practitioner is able to grasp the inflow cannula and direct it to the pump pocket for connection to the pump. When tunneling through the intercostal space, surgeons may resort to general surgical tools at their disposal, such as an anastomotic clamp or forceps. However, such tools may tear or otherwise injure the intercostal tissue when being forced into the intercostal space. Moreover, due to the high amount of force required to tunnel through the intercostal muscle, there is a risk of harming the patient, such as rupturing a vessel. Alternatively, surgeons may use a tunneling device to tunnel through the intercostal space. However, such tools must be able to securely grasp the inflow cannula and direct it to the pump pocket, while still being able to easily disconnect from the inflow cannula so that it may be connected to the pump. Therefore, there is a need in the art for a system and method which allows for a more controlled procedure of connecting a blood pump with the necessary tubing.

SUMMARY

It is therefore desirable to provide a system and method that allows for connection of a cannula and a blood pump in a controlled manner. Furthermore, rather than relegating the practitioner to grasping the proximal end of the cannula as described above, it is desirable to provide the cannula and other system components with features on, as a part of, or insertable into the cannula and other components, that allow for a connection between the cannula and the blood pump. To that end, a system for facilitating fluid connection between a blood pump and a circulatory system of a patient is provided. The system includes a cannula having proximal and distal ends. The distal end of the cannula adapted to be in fluid communication with the circulatory system. The proximal end of the cannula is configured to couple to an inlet of the blood pump. The system further includes a tunneling device configured to be inserted into a body of a patient to direct the proximal end of the cannula adjacent to the inlet for connection thereto. The cannula further includes a first connecting structure. The tunneling device further includes a second connecting structure. The first and second connecting structures are selectively engageable to allow in situ connection and disconnection between the cannula and tunneling device. In some embodiments, the first and second connecting structures are configured to frictionally secure one another in order to provide the selective engagement. For example, the frictional securement may be provided by features on one or both of the first or second connecting structures that provide a snap fit therebetween. In other embodiments, however, one or more separate elements, such as a loop of suture or other material, may be used to provide the selective engagement between the first and second connecting structures.

Another embodiment of a system for facilitating fluid connection between a blood pump and a circulatory system of a patient is provided. The system includes a cannula having proximal and distal ends. The distal end of the cannula is adapted to be in fluid communication with the circulatory system. The proximal end of the cannula is configured to couple to an inlet of the blood pump. The system further includes a plug configured to be inserted into the proximal end of the cannula and a tunneling device configured to be inserted into a body of a patient. The plug further includes a first connecting structure. The tunneling device further includes a second connecting structure. The first and second connecting structures are selectively engageable to allow in situ connection and disconnection between the cannula and tunneling device.

A method of facilitating fluid connection between a blood pump and a circulatory system of a patient is also provided. The method includes directing a distal end of a cannula into fluid communication with the circulatory system. The method further includes inserting the blood pump into a body of the patient and inserting a tunneling device into the body of the patient. The method further includes selectively engaging a first connecting structure of the cannula with a second connecting structure of the tunneling device and directing a proximal end of the cannula adjacent to an inlet of the blood pump. The method further includes connecting the proximal end of the cannula to the inlet.

In one embodiment, a system for facilitating fluid connection between a blood pump and a circulatory system of a patient is provided and includes a cannula, a tunneling device, and a plug. The cannula has proximal and distal ends. The distal end of the cannula is adapted to be in fluid communication with the circulatory system, and the proximal end of the cannula configured to couple to an inlet of the blood pump. The tunneling device is configured to be inserted into a body of a patient to direct the proximal end of the cannula adjacent to the inlet for connection thereto, and the tunneling device has a first connecting structure. The plug includes a first plug part and a second plug part. The first plug part has a second connecting structure, and the second plug part is configured to be inserted in the proximal end of the cannula. The first and second connecting structures are selectively engageable to allow in situ connection between the cannula and tunneling device. The first and second plug parts are selectively disengageable to allow in situ disconnection between the cannula and the tunneling device when the proximal end of the cannula is adjacent to the inlet.

Methods of facilitating fluid connection between a blood pump and a circulatory system of a patient using a system are also disclosed.

Various additional objectives, advantages, and features of the invention will be appreciated from a review of the following detailed description of the illustrative embodiments taken in conjunction with the accompanying drawings.

BRIEF DESCRIPTION OF THE DRAWINGS

FIGS. 1B through 1D are diagrammatic views of different steps associated with facilitating a connection between a cannula and the blood pump.

FIGS. 14A and 14B show an alternative manner of engagement between a tunneling device and a cannula plug.

FIGS. 15A and 15B show yet another alternative manner of engagement between a tunneling device and a cannula plug.

FIGS. 16A-16D show yet another alternative manner of engagement between a tunneling device and a cannula plug.

FIGS. 17A-17D show yet another alternative manner of engagement between a tunneling device and a cannula plug.

FIGS. 18A-C are elevation views showing one manner of engagement between a tunneling device and a cannula plug according to one embodiment of the invention, with the cannula plug shown in cross-section.

FIGS. 19A-C are elevation views showing another manner of engagement between a tunneling device and a cannula plug according to one embodiment of the invention, with the cannula plug shown in cross-section.

FIG. 20 is a perspective view of a first plug part and a second plug part according to the embodiment of FIG. 19A.

DETAILED DESCRIPTION

Figure 1A:
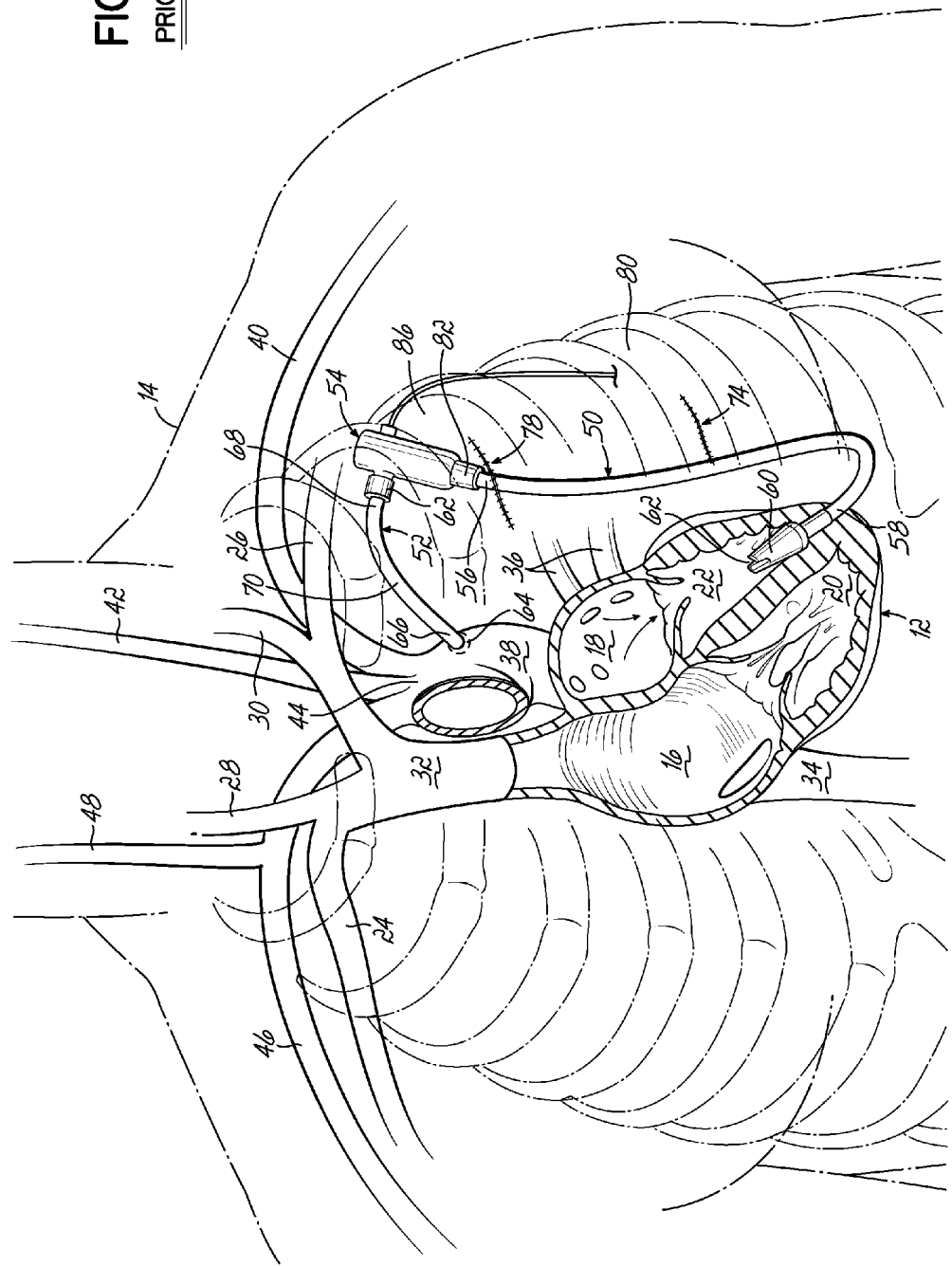
FIG. 1A is a diagrammatic view of a circulatory assist system, including a blood pump and multiple cannulae, in accordance with one embodiment of the invention, with the heart of a patient shown in partial cross-section.
Figure 1C:
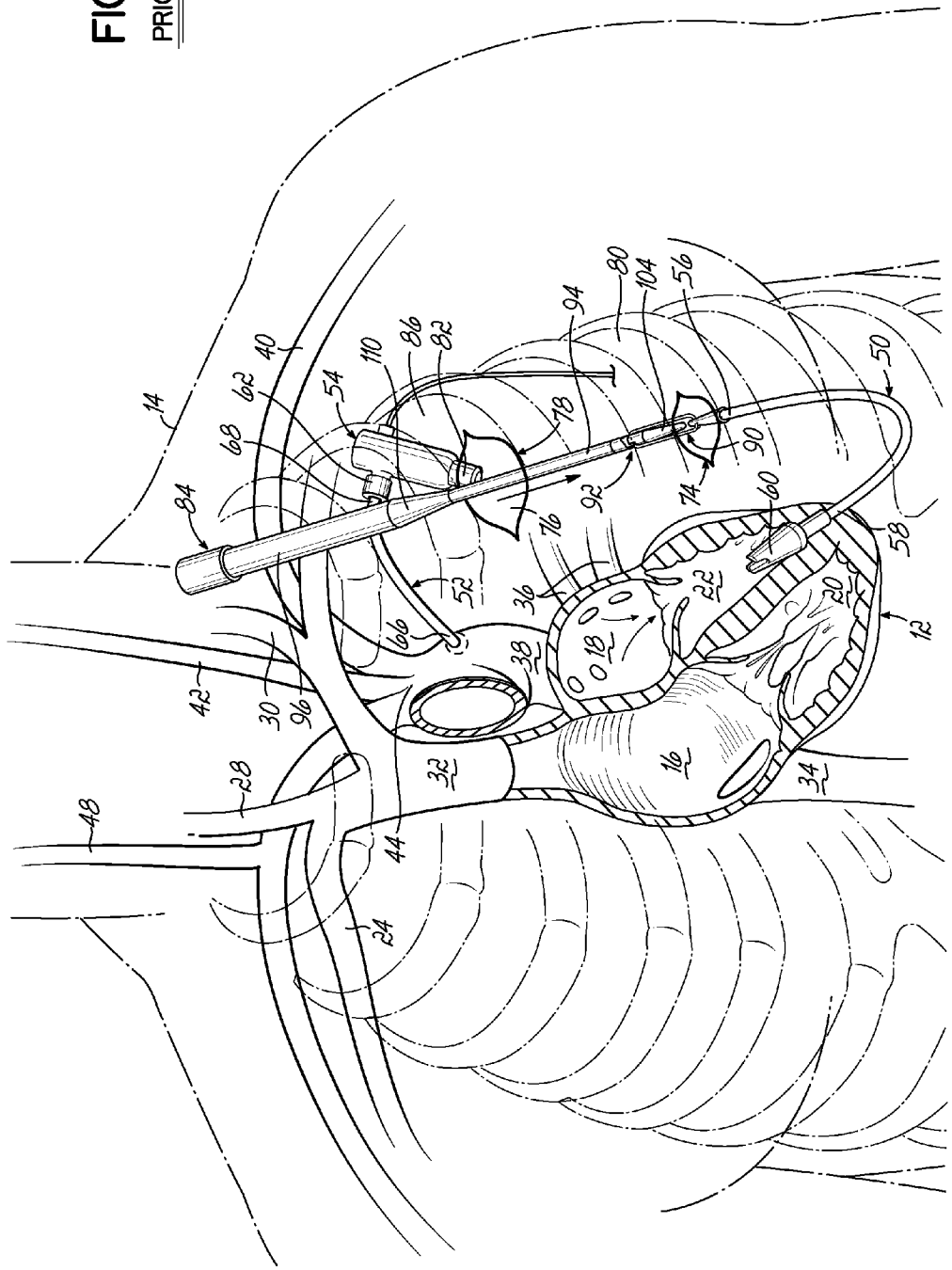
Figure 1D:
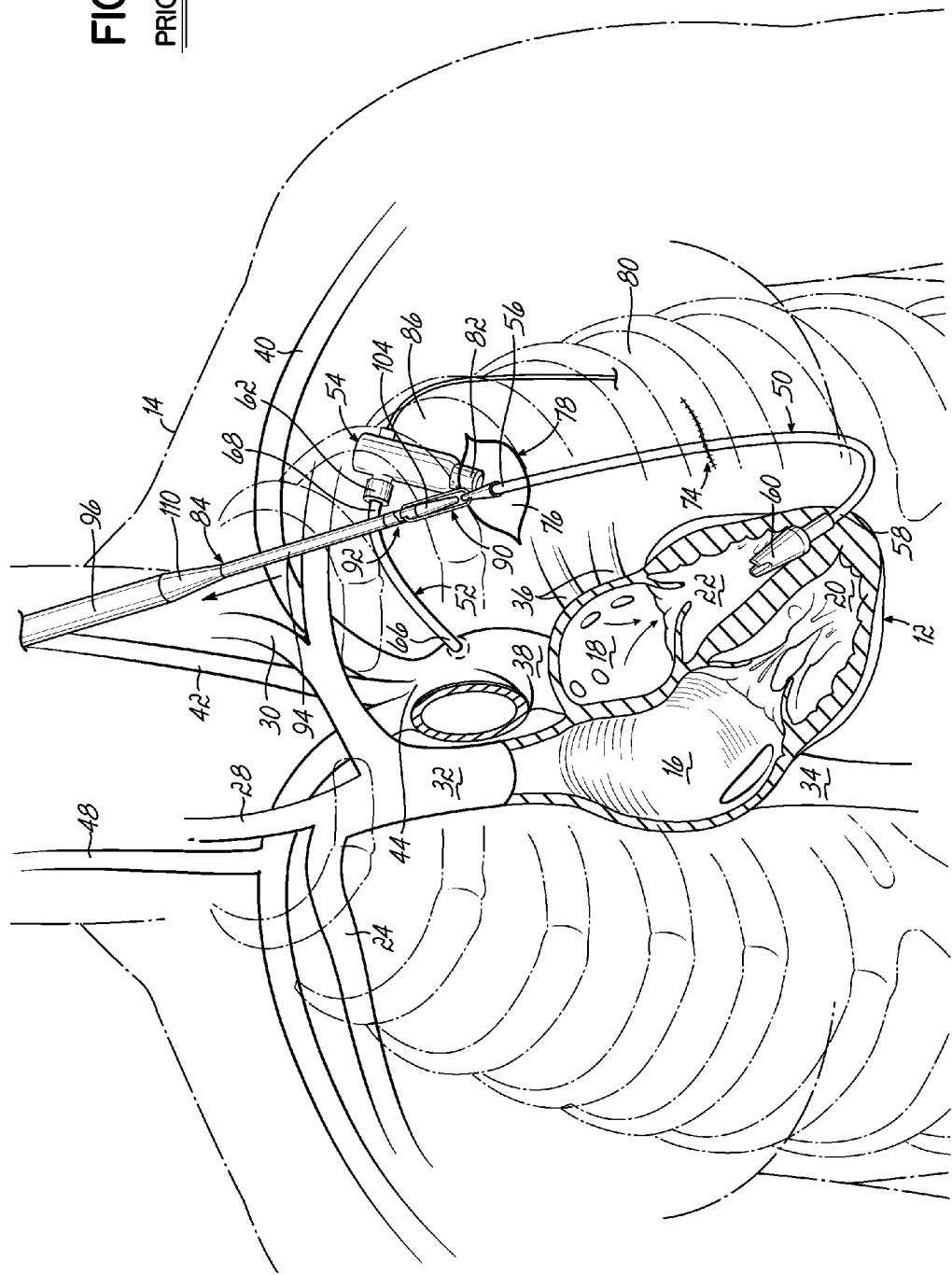

With respect to FIG. 1A, for illustrative purposes, certain anatomy is shown including the heart 12 of the patient 14 having a right atrium 16, a left atrium 18, a right ventricle 20, and a left ventricle 22. Blood from the right and left subclavian veins 24, 26 and the right and left jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 via pulmonary veins 36 and is pumped into the left ventricle 22. Blood leaving the left ventricle 22 enters the aorta 38 and flows into the left subclavian artery 40, the left common carotid 42, and the brachiocephalic trunk 44, including the right subclavian artery 46 and the right common carotid 48.

Two cannulae 50, 52 (inflow and outflow, respectively) extend between cardiovascular structures and a pump 54, which may be any implantable or extracorporeal pump 54 that is radially- and/or axially-driven. Those skilled in this art, however, recognize that other types of pumps may be used in other embodiments but may include pumps such as those described in U.S. Pat. No. 8,157,720, which is incorporated herein by reference in its entirety, or commercially-available pumps, such as the SYNERGY Pocket Micro-Pump from CircuLite, Inc. (Saddle Brook, N.J.), which is capable of delivering blood flow at rates ranging from about 3 L/min to about 4 L/min.

The inflow cannula 50 may be any suitable intravascular cannula device constructed from materials, such as an extruded aliphatic, polycarbonate-base polyurethane; aliphatic polyether polyurethane; aromatic polyether polyurethane; aromatic polycarbonate based polyurethane; silicone modified polyurethane; or silicone. Antimicrobial agents may be embedded within the inflow cannula 50 material prior to the forming process to effectively reduce or eliminate the presence of a bio-film and reduce the potential for infection. Alternatively, the antimicrobial agent may be applied to the surface of the inflow cannula 50 after the molding process is complete.

A reinforcing structure (not shown) may be included in the inflow cannula 50 construction to reduce the likelihood of kink formation. The reinforcing structure may be, for example, a braided or coiled construction of a metal wire, such as stainless steel or Nitinol (nickel-titanium), or a polymeric material, such as KEVLAR (E.I. du Pont de Nemours and Co., Wilmington, Del.). The construction material may have various cross-sectional shapes, including, but not limited to, round and rectangular. If a round wire is used, the wire diameter may typically vary from about 0.001 inch (0.0254 mm) to about 0.005 inch (0.127 mm). If the material has a rectangular cross-section, the rectangle may typically have a height ranging from about 0.001 inch (0.0254 mm) to about 0.005 inch (0.127 mm) and a width ranging from about 0.003 inch (0.0762 mm) to about 0.010 inch (0.254 mm).

The inflow cannula 50 includes proximal and distal ends 56, 58. The distal end 58 of the inflow cannula 50 may include a tip 60, which is described in greater detail in U.S. patent application Ser. No. 13/025,757, which is incorporated herein by reference in its entirety. The illustrative tip 60 includes one or more openings 60 that extend proximally from a distal tip. The openings 60 permit the flow of blood from the left ventricle 22 into a lumen 75 of the inflow cannula 50 even in the event that the distal tip end becomes obstructed with tissue from within the left ventricle 22. The tip 60 may be constructed from a polished titanium or other suitable material and have a design that reduces fluidic turbulence and the risk of thrombosis formation. The tip design may also facilitate the coupling of the tip 60 to the distal end 58 of the inflow cannula 50. For example, in some embodiments, a proximal end of the tip 60 may include one or more barbs (not shown) to provide resistance against undesired removal of the tip 60 from the inflow cannula 50.

The outflow cannula 52 extends from an outflow port or outlet 62 of the pump 54 to an arterial access site 64, which is illustrated herein as within the aorta 38. The outflow cannula 52 may include a construction that is generally similar to the inflow cannula 50; however, a distal end 66 of the outflow cannula 52 is configured to be secured to the arterial access site 64. Accordingly, the distal end 66 may be secured by one or more sutures and/or include one or more anastomotic connectors (not shown), such as those taught in U.S. patent application Ser. No. 12/829,425, the disclosure of which is incorporated herein by reference, in its entirety. The outflow cannula 52 may be tapered distally, similar to the inflow cannula 50, so that a proximal end 68 has a larger diameter that accommodates the outflow port 62 of the pump 54 and a smaller diameter cannula body 70 accommodates the anatomy of the patient 14. Again, for exemplary purposes only, the proximal end 68 may have a diameter that ranges from about 8 mm to about 11 mm while the diameter of the cannula body 70 may range from about 3 mm to about 7 mm.

As shown in FIG. 1B, the practitioner has inserted a tip 60 of an inflow cannula 50 into a cavity of the heart 12, and more specifically, the left ventricle 22. Because much of the discussion hereinbelow focuses on inflow cannula 50, "inflow cannula" and "cannula" are used interchangeably herein and are meant to refer to reference numeral 50. In order to prevent blood from traveling through and out of the cannula 50, the proximal end of the cannula 50 includes a cannula plug 72. "Cannula plug" and "plug" are used interchangeably herein and are meant to refer to reference numeral 72. As shown, the physician has directed the remainder of the cannula 50 into through the thoracotomy incision 74 such that the cannula 50 is resting within the thoracic cavity 76. The thoracotomy as described herein may be a mini-thoracotomy, as understood by those skilled in the art, made at the fourth intercostal space 80. However, the thoracotomy as disclosed herein need not occur at the fourth intercostal space 80 and may occur elsewhere according to the characteristics of the patient as well as the preferences of the practitioner.

At this point, the practitioner also has inserted the pump 54 into the pump pocket 78, which may be subcutaneously or submuscularly situated. The steps involved in creating a pump pocket 78 will be apparent to those skilled in the art. Alternatively, the physician may create the pump pocket 78 on the patient, but may wait to insert the pump 54 into the pocket once connected to the cannula 50. The proximal end of the cannula 50 and the inlet or inflow port 82 of the pump 54 must then be connected in order to close the loop of the circulatory assist system.

In order to connect the cannula 50 with the pump 54 in situ, the practitioner may direct a tunneling device 84 through the pump pocket 78, further into an intercostal space, and into the thoracic cavity 76. As described herein, connecting or connection "in situ" is meant to describe connecting or connection inside the body, such as, for example, inside the thoracic cavity. The tunneling device 84 described herein is particularly advantageous for accessing the thoracic cavity 76 through an intercostal space. For this reason, the system and method is described herein with a frame of reference to such anatomical areas. The invention, however, is not limited to the chosen frame of reference and such descriptive terms, and may be utilized for accessing parts of a patient's body other than those shown. For example, the system 10 may be utilized wherever it is advantageous to use a tunneling device 84, including on the opposite side of the chest to that shown in FIGS. 1A-1E. More specifically, the system 10 may be utilized on the right side of the chest to support different methods and devices, such as those taught in U.S. patent application Ser. No. 12/144,738, the disclosure of which is incorporated herein by reference, in its entirety.

In one embodiment, the tunneling device 84 is directed through the second intercostal space 86. Therefore, in that embodiment, the pump pocket 78 may be situated such that the second intercostal space 86 is accessible, in order for the tunneling device 84 to be directed through the pump pocket 78, and into and through the second intercostal space 86. However, in other embodiments, the tunneling device 84 may be directed into a different intercostal space or at a different area of the body. Where the tunneling device 84 is directed into the body ultimately depends on the configuration of the tunneling device 84 and ancillary devices, as well as the position of the pump 54 and pump pocket 78. As described in more detail below, the tunneling device 84 is configured to be inserted into the body in a controlled manner by dilating, rather than tearing or otherwise injuring, the intercostal tissue. The tunneling device 84 is further configured to prevent damage to structures when being directed into the body. Once the tunneling device 84 is directed through the intercostal space, the practitioner may direct the tunneling device 84 further through the thoracic cavity 76 towards the proximal end 56 of the cannula 50. Then, once the distal end 88 of the tunneling device 84 is adjacent or near the proximal end 56 of the cannula 50, the practitioner may provide a connection between the tunneling device 84 and the cannula 50. As described in more detail below, the cannula 50 and the tunneling device 84 include connecting structures 90, 92 which allow for selective engagement between the cannula 50 and the tunneling device 84, which allow connection and disconnection between the cannula 50 and the tunneling device 84 within the body of the patient. Although the connecting structures allow for this, it is important to note that a user may decide to actually make the connection while at least a connecting portion of the cannula 50 is outside the body. More specifically, the cannula 50 includes a first connecting structure 90 and the tunneling device 84 includes a second connecting structure 92. In some embodiments, where a cannula plug 72 is inserted into the proximal end of the cannula 50, the first connecting structure 90, or a portion of the first connecting structure 90, may be included on, or as a part of, the cannula plug 72.

In order to connect the cannula 50 with the tunneling device 84, the practitioner may be required to reach into the thoracic cavity 76 to engage the first and second connecting structure 90, 92. Alternatively, where the proximal end 56 of the cannula 50 is residing exterior to the body, the practitioner may also direct the distal end 88 of the tunneling device 84 outside of the body, thereby allowing the practitioner to connect the cannula 50 and the tunneling device 84.

After connecting the cannula 50 and the tunneling device 84, the surgeon may retract the tunneling device 84 such that the cannula 50, connected with the tunneling device 84, is directed towards the pump pocket 78 where the pump 54 resides. Alternatively, instead of retracting the entire tunneling device 84, the tunneling device 84 may be configured such that a first elongate dilator 94 thereof may move relative to a second elongate dilator 96 (FIGS. 3 through 5B). As will be described in more detail below, the first elongate dilator 94, which may be connected to the cannula 50, may be retracted through a lumen 97 in the second elongate dilator 96, while the second elongate dilator 96 remains in its position dilating the intercostal space. In some embodiments, the cannula plug 72 is configured to dilate tissue. More specifically, as the tunneling device 84 is retracted further proximally such that the cannula plug 72 is entering the intercostal space, the cannula plug 72 will traverse the same path through the tissue. Once the cannula plug 72 dilates and traverses through the intercostal space, the proximal end of the cannula 50 is also directed through such that it is adjacent the inlet 82 of the blood pump 54. At this point, the pump 54 may be residing in the pump pocket 78 or may be residing out of the body. In order to communicate the proximal end of the cannula 50 with the inlet of the pump 54, the practitioner may remove the cannula plug 72.

In order to prevent blood from flowing from the proximal end of the cannula 50 once the cannula plug 72 is removed, the practitioner may clamp the cannula 50 at a point distal of the proximal end. After removing the cannula plug 72, the practitioner may then connect the proximal end 56 of the cannula 50 with the inlet of the pump 54, thereby closing the loop of the circulatory assist device. The practitioner may then unclamp the cannula 50 once the proximal end 56 thereof is connected with the inlet 82, as shown in FIG. 1A.

Figure 2:
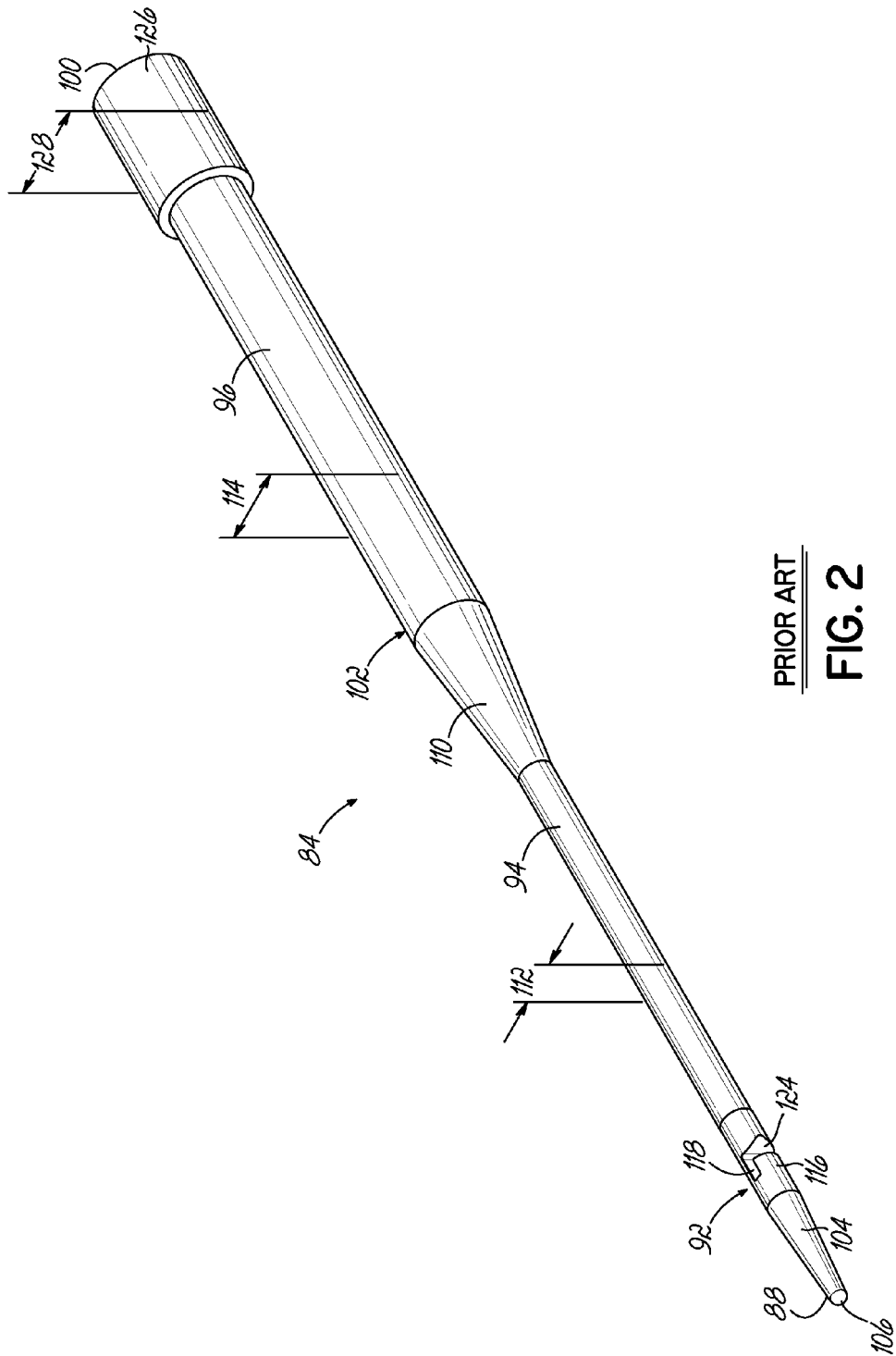
FIG. 2 is a perspective view of a tunneling device according to one embodiment of the invention.

One embodiment of a tunneling device 84 is shown in FIG. 2. The tunneling device 84 includes a proximal end 100, a distal end 88, and a shaft 102 therebetween. In the embodiment shown in FIG. 2, the tunneling device 84 is a unitary member such that relative movement between the different portions is not provided. At least part of the tunneling device 84 is defined as a dilator including a first elongate dilator 94, and a second elongate dilator 96 situated proximal of the first elongate dilator 94. As shown in FIG. 2, the tunneling device 84 further includes a distal, tapered tip 104 having a rounded end 106. The tapered tip 104 and rounded end 106 are provided in order to gently dilate, rather than tear or otherwise injure, the intercostal space when directed into the body. In some embodiments, the first and second elongate dilators 94, 96 have a constant diameter along their lengths. The first elongate dilator 94 has a first diameter 112 and the second elongate dilator 96 has a second diameter 114. The second diameter 114 is larger than the first diameter 112. In other embodiments, however, the first and second elongate dilators 94, 96 may not have a constant diameter along their lengths. For example, only one of the first or second elongate dilators 94, 96 may have a constant diameter along their lengths. Alternatively, one or both of the first and second elongate dilators 94, 96 may be tapered along their lengths such that the diameters of each increase along their lengths. Moreover, the tunneling device 84 may be defined by more or less than two elongate dilators. For example, the tunneling device 84 may be tapered along the entire length such that the tunneling device 84 is defined as simply one elongate dilator. On the other hand, the tunneling device 84 may be defined as more than two elongate dilators, having tapered sections between each, like the tapered section 110 shown in FIG. 2.

When directed into the intercostal space, the first elongate dilator 94 dilates the tissue to a first stage. As the tunneling device 84 is further directed into the thoracic cavity 76 to a point where the second elongate dilator 96 resides in the intercostal space, the tissue is dilated to a second stage. Depending on the anatomical characteristics of the patient and dimensions of the tunneling device 84, during the second stage of dilation, the first elongate dilator 94 may reside within the thoracic cavity 76, while a portion of the second elongate dilator 96 is enveloped by intercostal tissue. The distance into the body that the tunneling device 84 must traverse in order to be connected to the cannula 50 depends in part on the length of the tunneling device 84, the location of the cannula 50, and the anatomy of the patient 14.

To provide for a more efficacious transition between the first and second stages of dilation, there is a tapered section 110 between the first and second elongate dilators 94, 96. The tapered section 110 includes a generally frustroconical shape and is configured such that there is a constant increase in diameter between the first and second elongate dilators 94, 96. However, the tapered section 110 need not be configured such that the diameter increases at a constant rate. The tapered section 110 is provided to gradually dilate an opening in tissue as a practitioner inserts the tunneling device 84 further into the body of a patient 14, from the first stage of dilation to the second stage of dilation. More specifically, the tapered section 110 is provided to gradually dilate the tissue when the surgeon advances the tunneling device 84 from a position where the tissue envelops the first elongate dilator 94 to a position where the tissue envelops the second elongate dilator 96.

In one embodiment, the first diameter 112 (of the first elongate dilator 94) is between 3 and 6 mm, while the second diameter 114 (of the second elongate dilator 96) is between 12 and 18 mm. The total length of the tunneling device 84 may be approximately 270-330 mm, but may be shorter or longer, depending on the desired characteristics of the tunneling device 84, which may ultimately depend on the anatomy of the patient. The tapered tip 104 in one embodiment is included as a unitary part of the tunneling device 84

Figure 3:
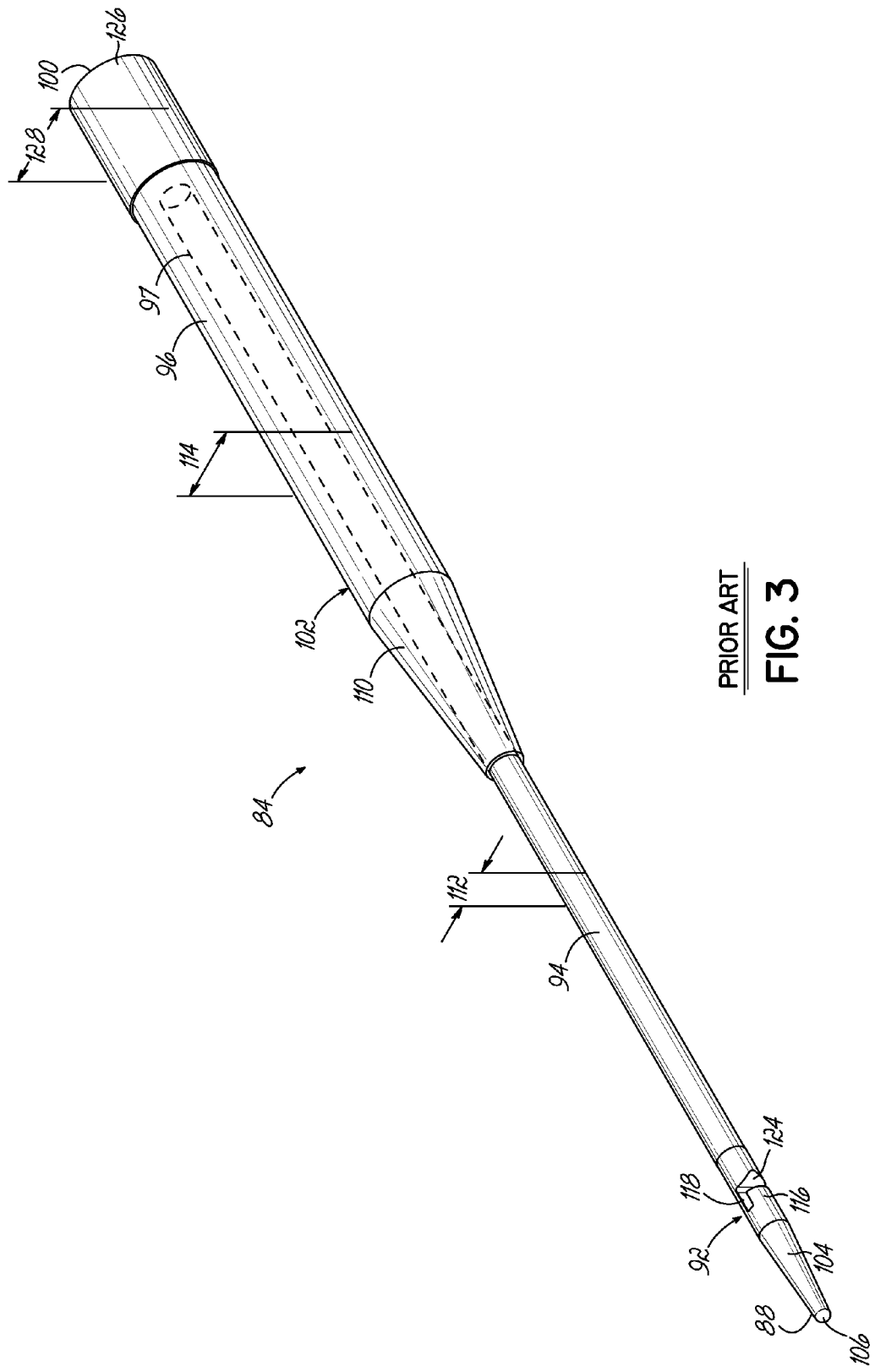
FIG. 3 is a perspective view of a tunneling device according to an alternative embodiment of the invention.
Figure 4:
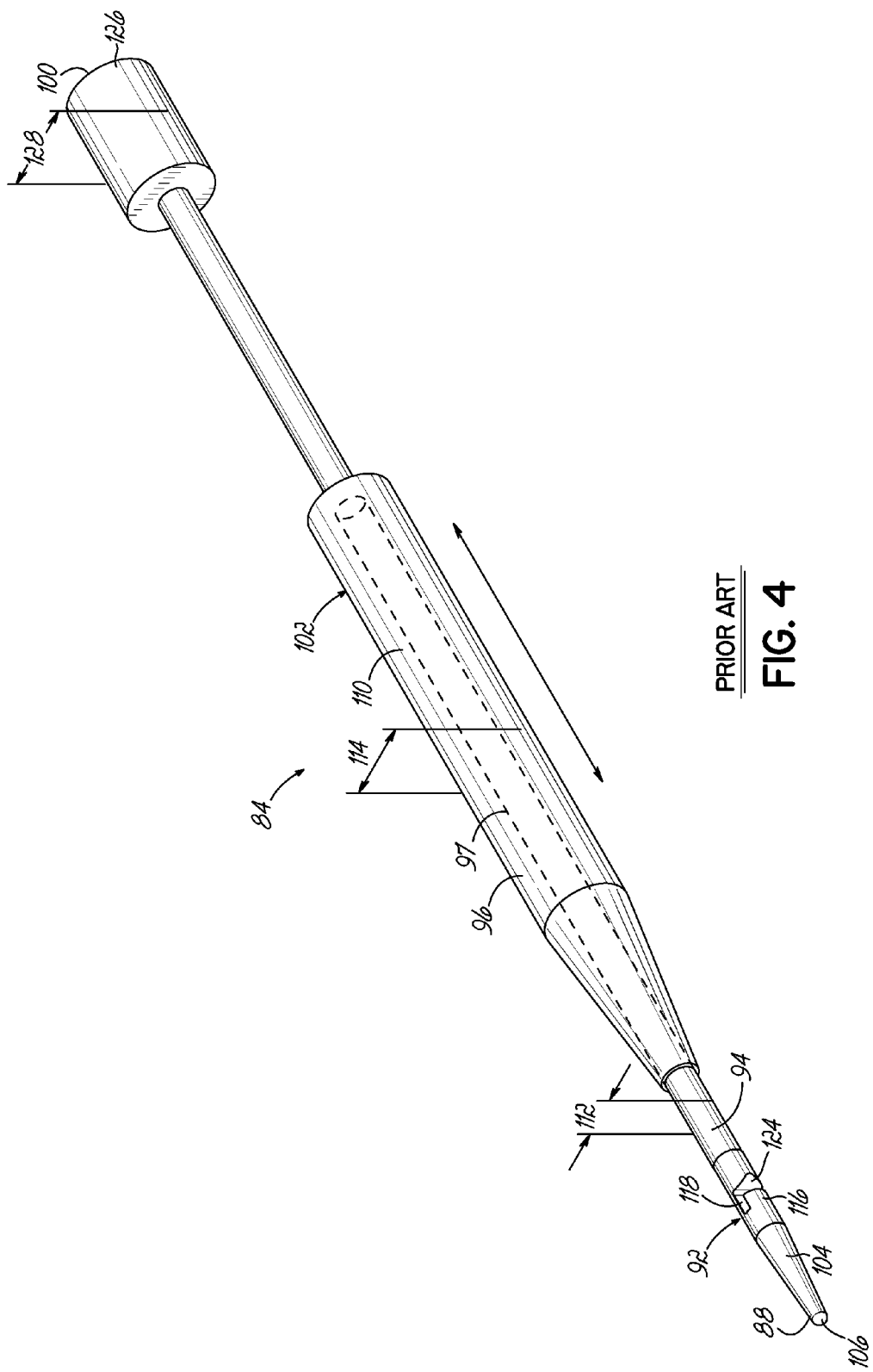
FIG. 4 is a perspective view of the tunneling device of FIG. 3 showing relative movement between components.

(FIG. 2) and as a unitary part with the first elongate dilator 94 (FIGS. 3 & 4). In alternative embodiments, however, the tapered tip 104, and potentially the second connecting structure 92, may be disconnectable from the first elongate dilator 94. Providing such a feature would allow a practitioner to interchange the dilating tip 104 and/or the second connecting structure 92, depending on the desire of the practitioner, as well as the availability of or compatibility with certain corresponding first connecting structures 90, as described below.

The tunneling device 84 may be provided with enough stiffness in order to pierce and traverse the intercostal tissue without buckling a substantial amount, but with enough flexibility to flex, or be diverted away, when contacting a relatively solid structure, such as bone. Moreover, the tapered tip 104 may be configured to push aside soft tissue, such as vessels, in order to produce a minimal amount of trauma, or no trauma at all. The tunneling device 84 may possess a durometer between 40D and 75D. The tunneling device 84 may be one material of the same material properties throughout. In other words, the entire tunneling device 84 may be of the same material having a single stiffness, for example. On the other hand, the tunneling device 84 may include different materials and/or characteristics along the length. For example, the tapered tip 104 may have different materials and/or characteristics than the first elongate dilator 94, which may have different materials and/or characteristics than the second elongate dilator 96.

In some embodiments, the tunneling device 84 may comprise multiple layers (not shown), each of which may impart certain characteristics to the tunneling device 84. For example, the tunneling device 84 may include inner and outer layers. More specifically, for example, the inner layer may include a material which may impart a desired stiffness or flexibility, for example, to meet the desired characteristics described above when traversing the intercostal space. The outer layer may include a material to impart lubricity or another characteristic that may assist in traversing the intercostal tissue. However, the outer layer may also be provided to contribute to characteristics of the tunneling device 84, such as stiffness or flexibility.

In one embodiment, the tunneling device 84 may be reinforced (not shown) along at least a section thereof. The reinforced section may be provided along the entire length of the tunneling device 84 or, alternatively, only along a certain portion. In a non-unitary embodiment, either one or both of the first and second elongate dilators 94, 96 may include a reinforced portion along at least a portion of their lengths. The reinforced portion may include longitudinally disposed members, such as a polymeric, fabric or metallic monofilament, or a polymeric, fabric or metallic polyfilament. Further, or alternatively, the reinforced section may include coils embedded in the body of one or both of the first and second elongate dilators 94, 96. The coils may be helically wound along the length of the tunneling device 84. Alternatively, the coils may be separate members, situated concentrically relative to a center axis of the tunneling device 84 and spaced apart along the length of the tunneling device 84. Preferably, the reinforced section or sections may provide stiffness during a pushing and pulling motion while still providing the desired flexibility. To facilitate easier insertion and removal, the tunneling device 84 also may include a lubricious coating on at least a portion of one or both of the first and second elongate dilators 94, 96, as well on as the tapered tip 104.

Proximal of the tapered tip 104, there may be a second connecting structure 92. However, in some embodiments, a portion of the second connecting structure 92 may be on or within the tapered tip 104. The second connecting structure 92 in the embodiments shown in FIGS. 2-4 and 8 is defined at least in part by a hook 116. The hook 116 is further defined by a generally L-shaped void 118 from the body of the first elongate dilator 94. The hook 116 is configured to engage with a first connecting structure 90 (i.e., FIG. 13). The first connecting structure 90 may be defined in part by a loop 120 (FIG. 13) of a suture or other material that is coupled to, for example, an aperture 122 of the cannula plug 72, which may be defined as the remaining part of the first connecting structure 90. However, the first connecting structure 90 may also be defined by only a portion of the cannula plug 72 (or void therein, such as the aperture 122 or cavity) that is selectively engageable with the second connecting element. The hook 116 may include a chamfer 124 to ease the connection with at least a portion of the first connecting structure 90, such as the loop 120 of suture or other material. The hook 116 may be reinforced, for example, by providing supplemental material thereon (not shown), or simply by providing more amount of material at or near the hook 116.

At the proximal end 100 of the tunneling device 84, there may be a knob or handle 126 provided in order to assist the user in gripping the tunneling device 84 during use. In the embodiments shown, the knob or handle 126 member is a cylindrical extension of the shaft 102 having a third diameter 128. As shown, the third diameter 128 is larger than the first and second diameters 112, 114. In alternative embodiments, however, the knob or handle 126 may be shaped or sized in a different manner than that shown in FIG. 2. The diameter of the knob as shown may be between 15 and 21 mm. Further, the knob or handle 126 may include a larger diameter than that shown, or may be situated transversely relative to the tunneling device 84, rather than concentrically, as shown. Alternative handle or knob members may be included in order to provide an ergonomic experience for the practitioner. Alternatively, in other embodiments, a handle 126 may not be provided.

As shown in FIGS. 3, 4, 5A & 5B, the tunneling device 84 may include multiple components which are movable relative to one another. To that end, the first and second elongate dilators 94, 96 are separate, nested components, such that the second elongate dilator 96 includes a lumen 97 (shown in hidden lines) for receiving the first elongate dilator 94. Notably, the knob or handle 126 is provided at the proximal end 134 of the first elongate dilator 94.

Relative movement between the first and second elongate dilators 94, 96 may be advantageous in certain situations. For example, when directing the cannula 50 to the pump pocket 78 for connection to the pump inlet 82, as described above, it may be advantageous to allow relative movement between the first and second elongate dilators 94, 96. In that situation, the second elongate dilator 96 may remain within the intercostal space for dilation, as the first elongate dilator 94 is retracted through the lumen of the second elongate dilator 96 to direct the cannula 50 adjacent to the inlet. However, when the practitioner is directing the tunneling device 84 into (or out from) the intercostal space, it may be advantageous to prevent the relative movement between the first and second elongate dilators 94, 96. To that end, a locking mechanism 130 for preventing relative movement between the first and second elongate dilators 94, 96 may be provided.

Figure 5A:
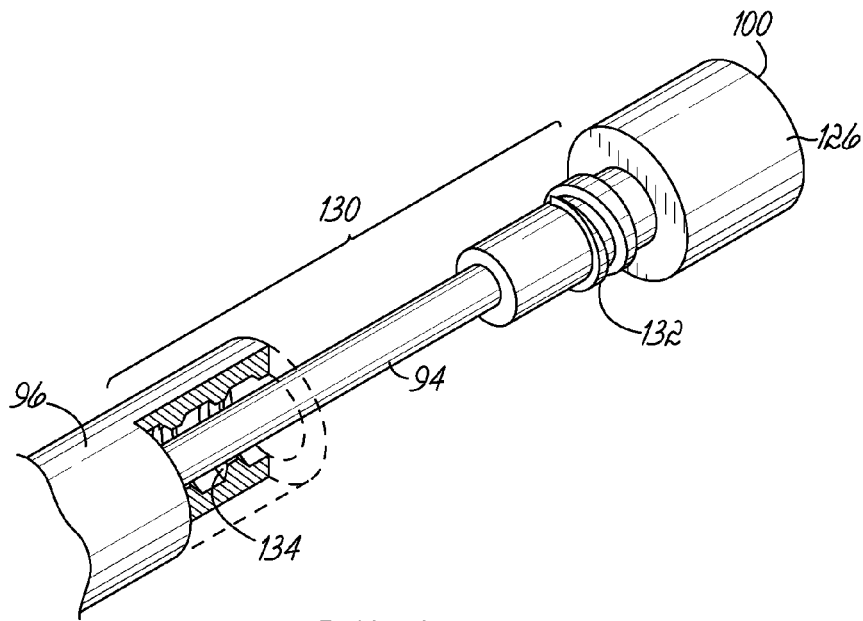
FIGS. 5A and 5B are perspective views showing different embodiments of locking mechanisms of the embodiment of FIG. 3 to prevent relative movement between components.
Figure 5B:
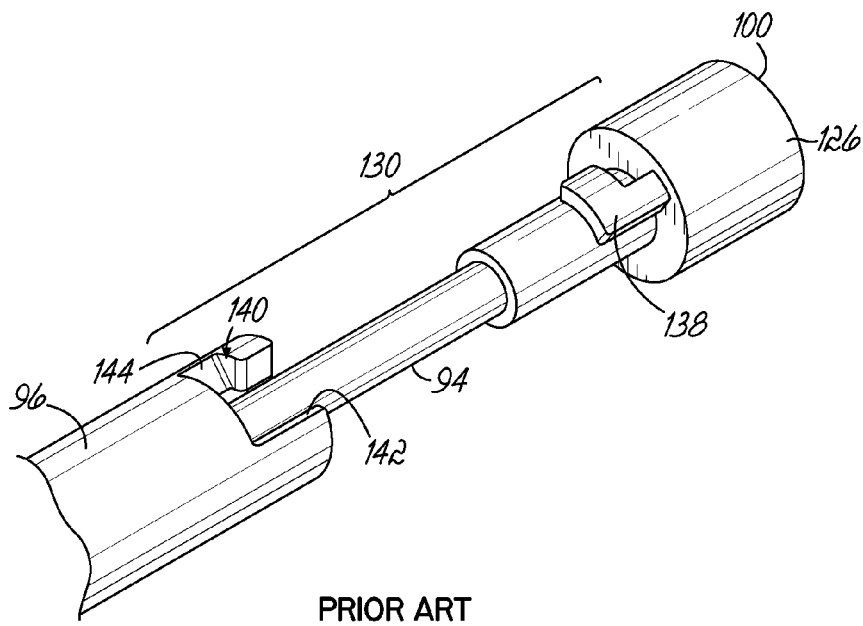

With reference to FIG. 5A, the locking mechanism 130 includes a first threaded section 132 adjacent the proximal end 100 of the first elongate dilator 94. The second elongate dilator 96 includes a second threaded section 134, which is complementary to the first threaded section 132 such that the first and second threaded sections 132, 134 may threadably engage one another. In an alternative embodiment, as shown in FIG. 5B, the first elongate dilator 94 includes an L-shaped protrusion adjacent the proximal end 134 of the first elongate dilator 94. The L-shaped protrusion 138 is configured to be accepted into L-shaped slot 140 of the second elongate dilator 96. In order to prevent relative movement between the first and second elongate dilators 94, 96, the protrusion 138 must be directed into the first portion 142 of L-shaped slot 140 and rotated into and in engagement with the second, lateral portion 144. The locking mechanisms 130 as shown in FIGS. 5A and 5B, and as described in this disclosure are meant to be illustrative. It is anticipated that alternative designs of locking mechanisms 130 are possible.

Figure 6:
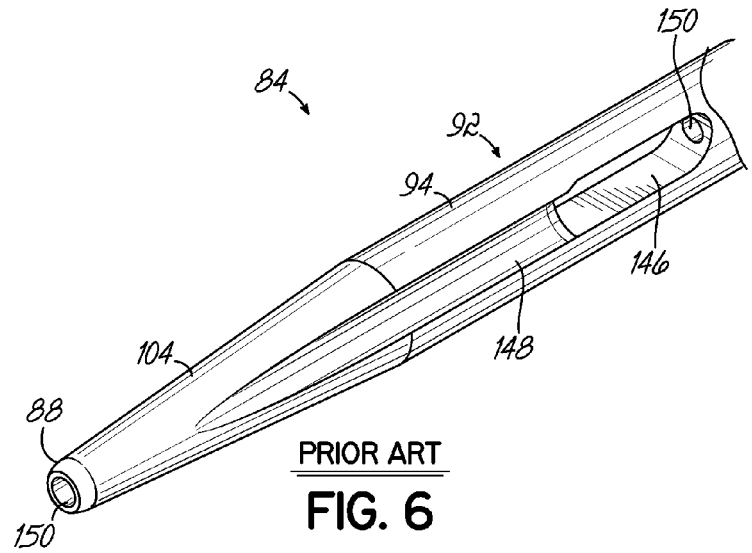
FIGS. 6 through 9 are detailed perspective views of various embodiments of second connecting structures of tunneling devices, such as those shown in FIGS. 2 and 3.

The distal end 88 of a tunneling device 84, including different embodiments of second connecting structures 92, are shown in FIGS. 6 through 9. The tunneling device 84 shown in FIGS. 6 and 7 includes an elongate aperture 146 configured to engage with at least a portion of a first connecting structure 90 connected to the cannula 50 or cannula plug 72, such as a loop 120 of suture, umbilical tape, or other material. The elongate shape of the aperture 146 is provided so that the practitioner may provide an easy, quick connection, such as when tying a loop 120 of suture or other material thereto. The elongate shape provides further advantages, such as providing a space for at least part of the loop 120 to reside as the first elongate dilator 94 is retracted through the lumen 97 of the second elongate dilator 96, as described above. The elongate aperture 146 of FIG. 6 is shown to be more proximally oriented than the elongate aperture 146 of FIG. 7. This may be for providing additional space for the loop 120 to reside during retraction. More specifically, the tunneling device 84 may optionally include at least one elongate recess 148 adjacent the elongate aperture 146. In some embodiments, two diametrically opposed elongate recesses 148 are provided.

Figure 7:
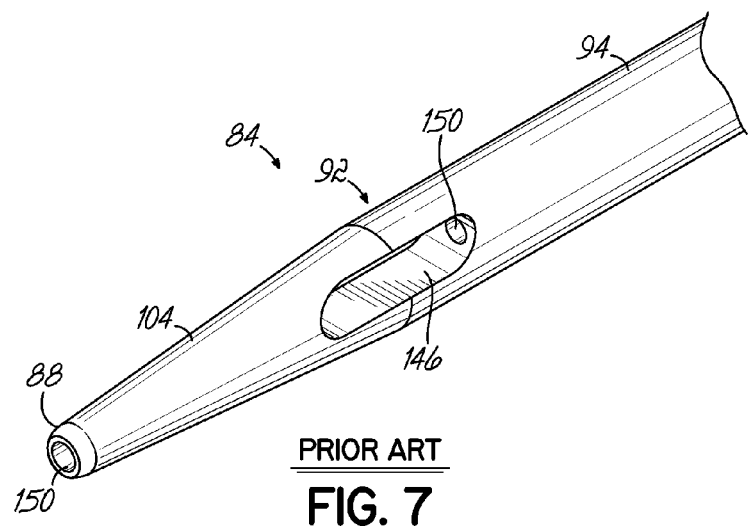

While the various embodiments of tunneling device 84 described herein may be directed into the body without the use of a guidewire, it may be advantageous in some patients to utilize a guidewire to provide initial access to the body. The use of a guidewire to access the body will be well understood by those skilled in the art. Therefore, an optional guidewire lumen 150 may be provided. The optional guidewire lumen 150 is shown in the embodiments of FIGS. 6 and 7. However, it is anticipated that any of the embodiments of a tunneling device 84 as described herein may include a guidewire lumen 150.

Figure 10:
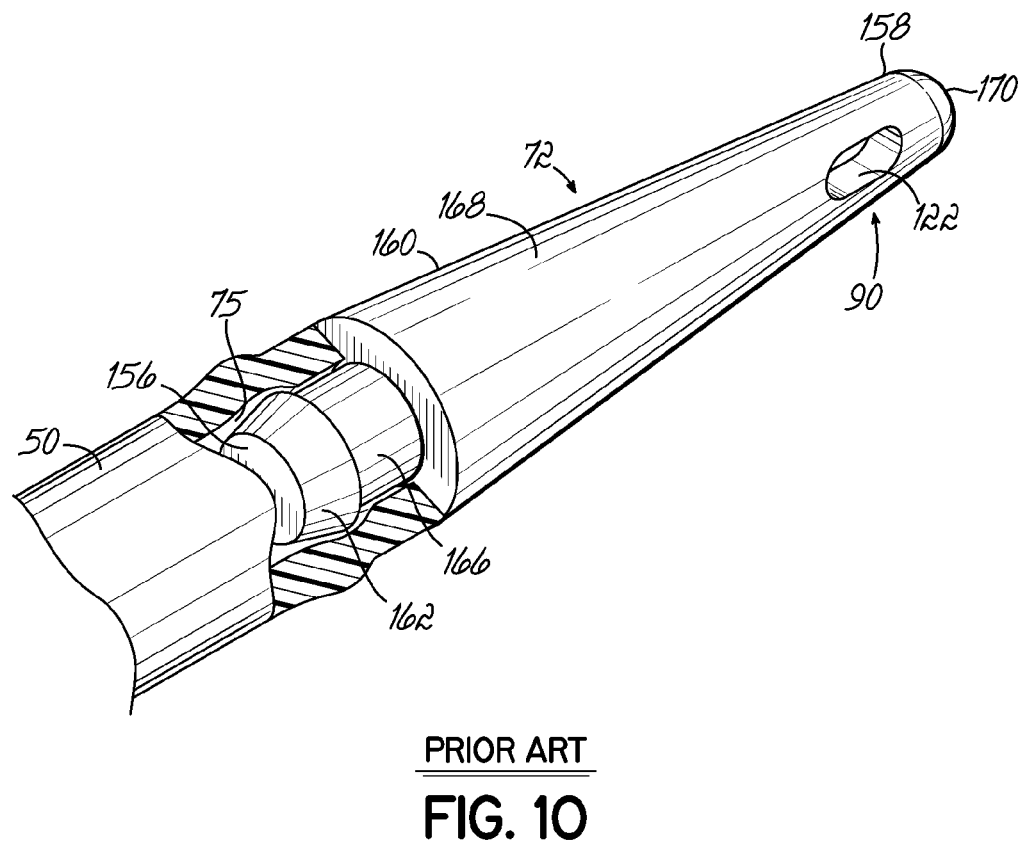
FIGS. 10 through 12 are perspective views of various additional embodiments of cannula plugs.
Figure 11:
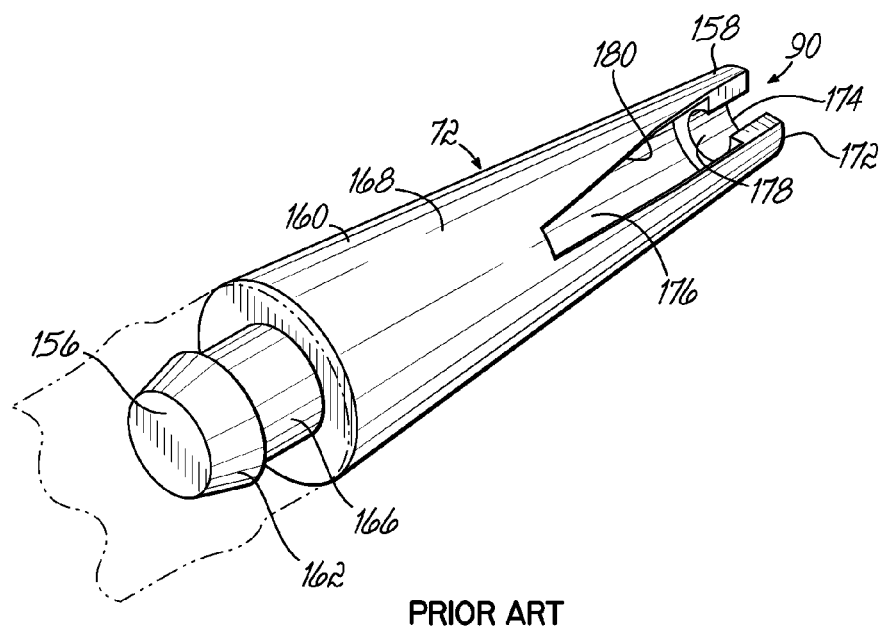
Figure 12:
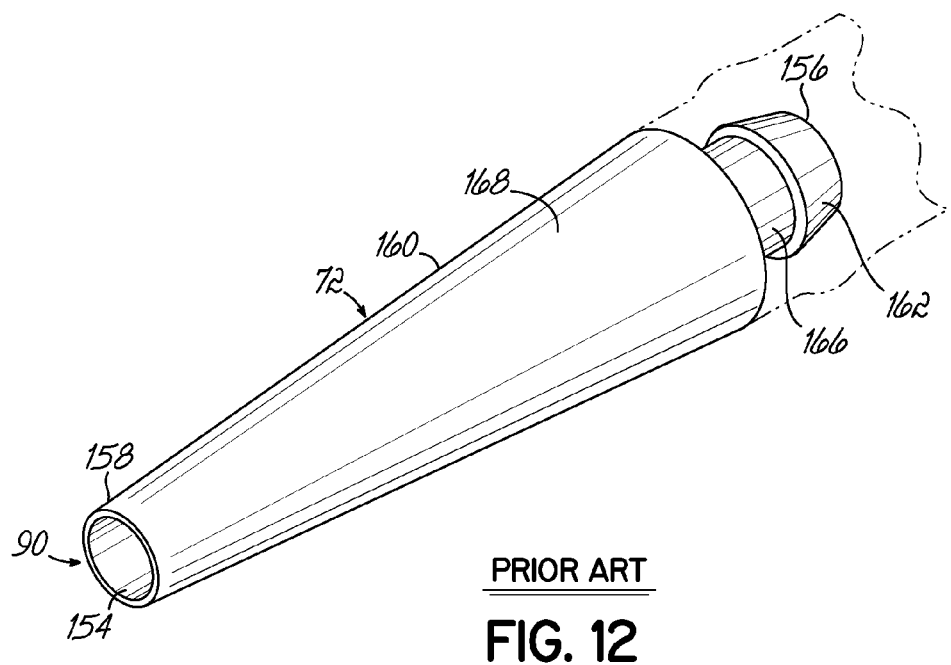

With reference to FIGS. 10 through 12, each of the cannula plugs 72 shown includes a proximal end 156, a distal end 158, and a body 160 therebetween. At the proximal end 156 of the cannula plug 72 is a stopper member 162. The stopper member 162 has a tapered, generally frustroconical shape that allows a practitioner to more easily insert the stopper member 162 into the lumen 75 of the cannula 50. In some embodiments, it may be provided that the stopper member 162 is configured to block flow of fluid from and seal the proximal end 56 of the cannula 50. The shape and configuration of the stopper member 162 as shown is but one embodiment, and it is appreciated that different shapes and configurations of the stopper member 162 that provide ease of insertion into the cannula 50 are possible. Preferably, the stopper member 162 engages the lumen 75 of the cannula 50 with an amount of interference and frictional force sufficient to prevent the unwanted removal of the cannula plug 72 from the cannula 50 during use. As discussed in more detail below, the cannula plug 72 includes features that may reduce the force required for traversing the cannula plug 72 through the intercostal tissue. These features therefore may reduce the likelihood of the unwanted removal of the cannula plug 72 from the cannula lumen 75. Extending distally from the stopper member 162 is a generally cylindrical portion, or a neck 166, having a smaller outer diameter than the stopper member 162. The configuration of the neck 166 may provide an ease of removal benefit once the practitioner desires to remove the cannula plug 72 from the cannula 50.

Figure 13:
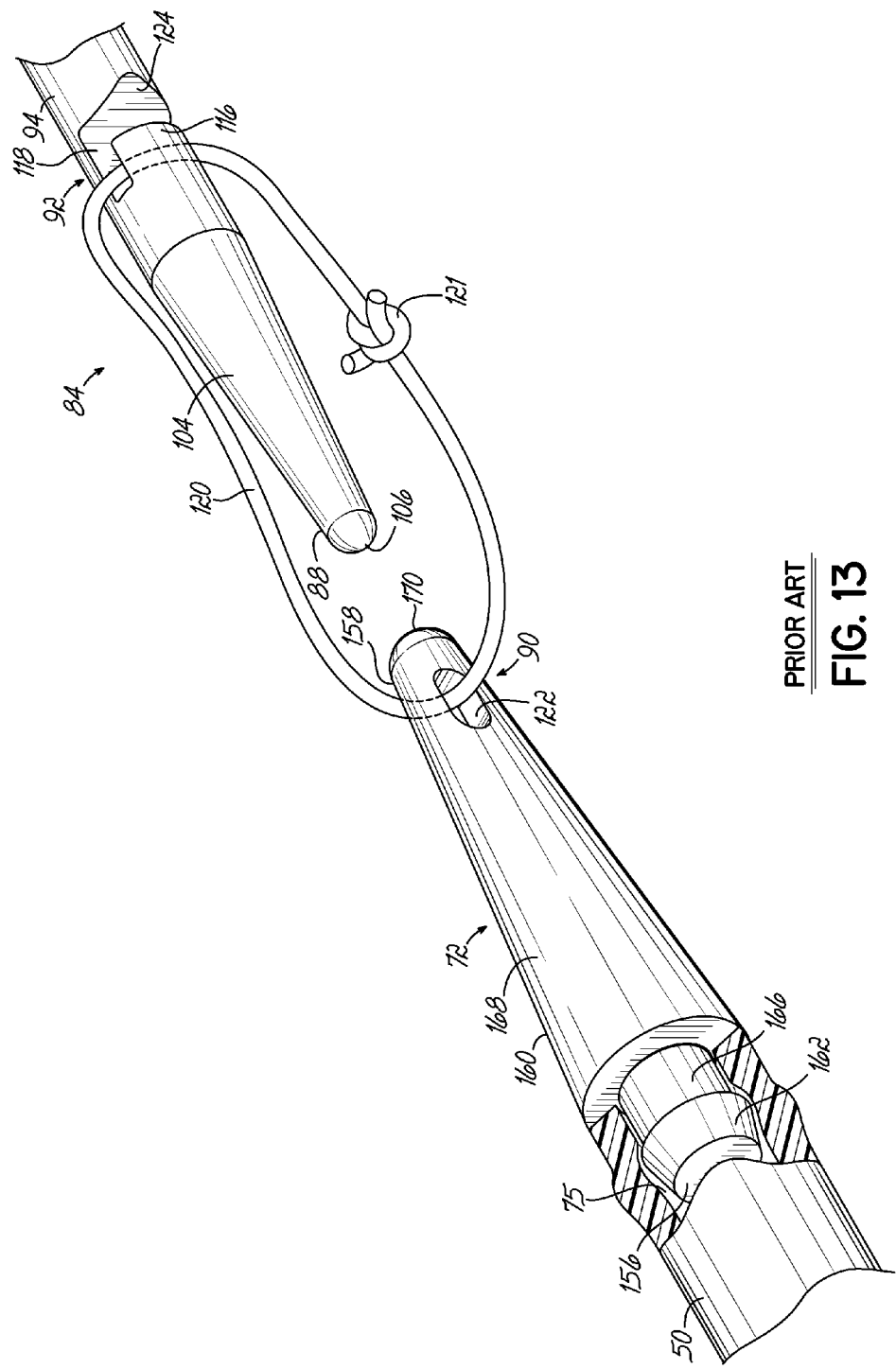
FIG. 13 is a perspective view showing one manner of engagement between a tunneling device and a cannula plug.

Further distal along the body of the cannula plug 72, there is an elongate frustroconical member 168. In FIGS. 10 and 13, the elongate frustroconical member 168 includes an aperture 122 near the distal end. As discussed herein, the aperture 122 may be provided as part of a first connecting structure 90 in order to selectively engage with a second connecting structure 92. The loop 120 may be considered as a part of one of the first or second connection structures 90, 92, or as a part of both. As discussed above, once the first and second connecting structures 90, 92 are engaged, the cannula 50 and the tunneling device 84 are connected and the cannula 50 may be directed adjacent the inlet of the pump 54 in the pump pocket 78.

FIG. 13 shows an embodiment where a separate element, such as the loop 120, is provided for engagement between the first and second connecting structures 90, 92. More specifically, loop 120 may be engaged with the aperture 122 and the hook 116, thereby connecting the cannula 50 and the tunneling device 84. In an alternative embodiment, the first connecting structure 90 may be a hook, while the second connecting structure 92 may be an aperture. Alternatively, both the first and second connecting structures may be an aperture, similar or identical to aperture 122. Furthermore, as shown, the loop 120 includes a knot 121. In some embodiments, the loop 120 may be prepackaged as an assembly with the cannula plug 72 such that the loop 120 is tied and engaged with the aperture 122 before the operating setting, at the manufacturer. Alternatively, the practitioner may use a material such as suture, or any other material at his or her disposal, to tie the loop 120 in the operating theatre.

At the distal end 158, the cannula plug 72 includes a rounded, tapered tip 170. As the tunneling device 84 is retracted to direct the cannula 50 to the pump pocket 78, the cannula plug 72 must also traverse the tissue interior to the pump pocket 78, such as an adjacent intercostal space. The tapered tip 170 and the elongate frustroconical member 168 are configured to gently dilate, rather than tear or otherwise injure, the tissue as the cannula plug 72 traverses the intercostal space. Notably, the location of the tissue into which the tunneling device 84 is directed is the location where the cannula plug 72, and thus the cannula 50, may exit. In at least one of the embodiments of the system as described herein, the diameter of the largest portion of the elongate frustroconical member 168 corresponds with, or is substantially equal to, the diameter of the second elongate dilator 96 of the tunneling device 84. Providing the cannula plug 72 with a largest diameter substantially equal to that of the tunneling device 84 (not including the handle 126) may reduce the force required to direct the cannula plug 72 through the intercostal tissue, as the tissue will already have been dilated by the tunneling device 84. This benefit reduces the likelihood of the unwanted removal of the cannula plug 72 from the proximal end of the cannula 50 and also reduces trauma to the patient. The cannula plug 72 may also be provided with a lubricious coating in order to reduce the frictional forces associated with traversing the tissue.

Figure 8:
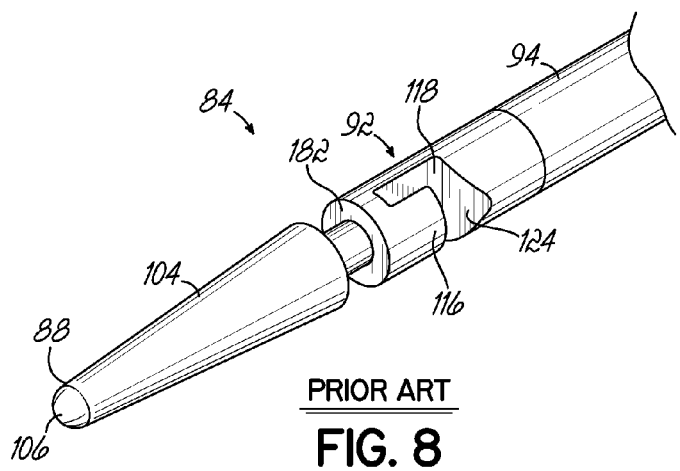

FIGS. 8, 14A, and 14B show one embodiment of the system where the first and second connecting structures 90, 92 are configured to frictionally engage one another. More specifically, the first and second connecting structures 90, 92 are configured to allow a snap fit therebetween. To that end, the distal end 172 of the elongate frustroconical member 168 includes an aperture 174 communicating with a cavity 176. The aperture 174, in combination with an opening 180, forms a penannular rib 178. The opening 180 is defined by a void of material along a portion of the circumference and the length of the elongate frustroconical member 168. The opening 180 is provided to impart resiliency characteristics upon the elongate frustroconical member 168. More specifically, with reference to FIGS. 14A and 14B, the distal end 88 of the tunneling device 84 is directed through the aperture 174 and into the cavity 176. The largest diameter (and potentially more proximally situated portions) of the tip 104 of the tunneling device 84 in the embodiment shown is larger than the diameter of the aperture 174. Therefore, the opening 180 is provided to allow the elongate frustroconical member 168 to resiliently expand to a flexed position (not shown) until the groove 182 of the tunneling device 84 mates with the rib 178 of the cannula plug 72, where the opening 180 of the elongate frustroconical member 168 is in a relaxed position (FIG. 14B). The outer diameter of the first elongate dilator 94 may be substantially equal to the largest outer diameter of the elongate frustroconical member 168. These diameters may be substantially equal in order to provide a smooth transition as the tunneling device 84 is retracted through the intercostal space to a point where the cannula plug 72 traverses the intercostal space. In each of the embodiments shown, the largest diameter of the elongate frustroconical member 168 corresponds with, or is substantially equal to, the diameter of the second elongate dilator 96 such that the intercostal tissue continues to be gently dilated as the cannula plug 72 traverses therethrough.

The resiliency and the shape of the opening 180 are also provided to allow for disconnection of the tunneling device 84 and cannula plug 72. More specifically, in order to disengage the tunneling device 84 and cannula plug 72, the practitioner may need to pull the distal end 88 of the tunneling device 84 towards the opening 180 such that the groove 182 may disengage from the rib 178. The practitioner may continue to pull the tunneling device 84 (and/or push the cannula plug 72) until the connection between the tunneling device 84 and the cannula plug 72 no longer exists.

Figure 9:
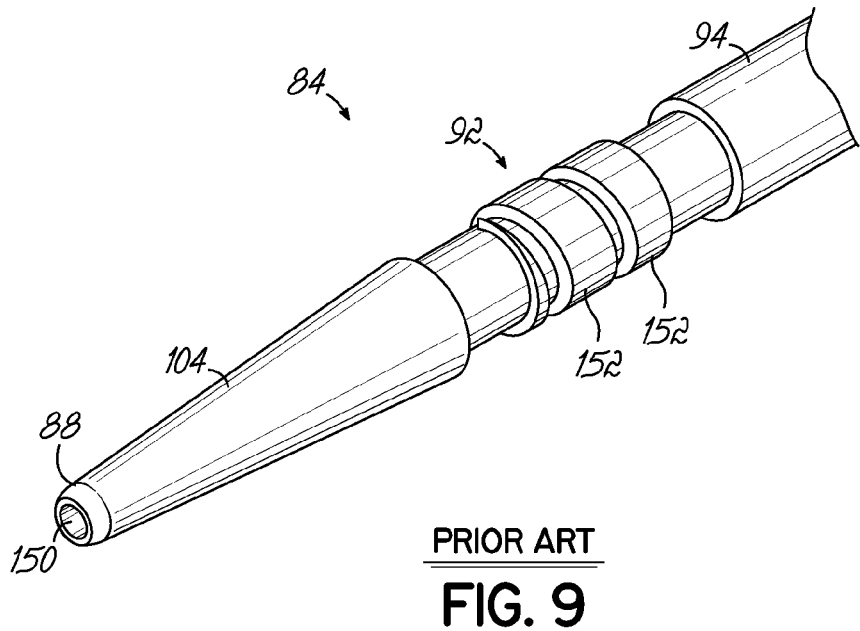

FIGS. 9, 15A, and 15B show another embodiment of the system where the first and second connecting structures 90, 92 are configured to frictionally engage one another. More specifically, the cavity 154 of the cannula plug 72 is configured receive and "grab," or frictionally secure the annular grooves 152 of the tunneling device 84. The annular grooves 152 may be molded into the first elongate dilator 94 as an integral component or, alternatively, may be a separately manufactured and added component. The annular grooves 152 are configured to be accepted into a cavity 154 of a cannula plug 72.

The cavity 154 may include an elastomeric material that is configured to allow the insertion of the tunneling device 84 therein. The material also is configured to prevent the removal of the tunneling device 84 from the aperture when the tunneling device 84 is retracted to direct the cannula 50 to the pump pocket 78. Such materials may include silicone or other elastomeric materials. The cannula plug 72 could be configured such that an inner portion including the cavity is an elastomeric material while the outer portion is a different material. Alternatively, the entire cannula plug 72 could comprise the elastomeric material. Notably, in the embodiment shown, at least the distal tip 104 may be removable from the tunneling device 84 in order to facilitate the interaction between the annular grooves 152 and the cavity 154.

Figure 16C:
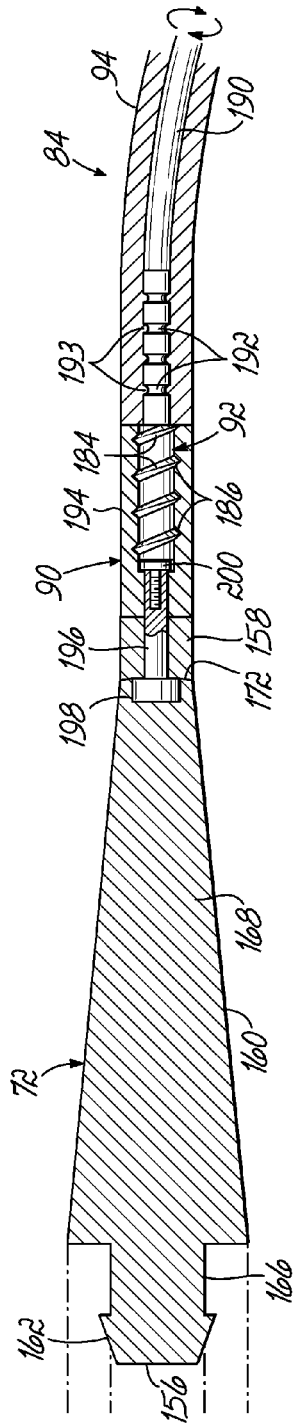

FIGS. 16A-16D show one embodiment of the system where the first and second connecting structures 90, 92 are configured to threadably engage, or interlock, one another. More specifically, the second connecting structure 92 may be defined in part by threads 184 and the first connecting structure 90 may be defined in part by threads 186 for mating with the threads 184 of the second connecting structure 92. Furthermore, the tunneling device 84 may include a detachable tip 104 having threads 188 for mating with the threads 184 of the second connecting structure 92. In this manner, a practitioner may direct the tunneling device 84 through a patient's intercostal space to a location proximate the cannula plug 72, as previously described and shown in FIG. 1B. Once the distal end 88 of the tunneling device 84 is adjacent or near the first connecting structure 90, the practitioner may remove the detachable tip 104 by disengaging the threads 188 of the detachable tip 104 from the threads 184 of the second connecting structure 92, as shown in FIG. 16A. The practitioner may then provide a connection between the tunneling device 84 and the cannula plug 72 by engaging the threads 186 of the first connecting structure 90 with the threads 184 of the second connecting structure 92, as illustrated in FIGS. 16B and 16C. This may be facilitated by an elongate member such as a cable 190 coupled with the second connecting structure 92 for providing selective rotation of the threads 184 of the second connecting structure 92. The cable 190 may also be coupled with the knob 126 (FIG. 16D) of the tunneling device 84 such that the practitioner may cause the rotation of the threads 184 by manually rotating the knob 126. The cable 190 may include annular grooves 192 that may engage with corresponding annular rings 193 for retaining the cable 190 within the tunneling device 84. In order to disengage the tunneling device 84 and the cannula plug 72, the practitioner may disengage the threads 184 from the threads 186. In the embodiment shown, threads 184 are external, or male, threads, while threads 186, 188 are internal, or female, threads. However, it should be appreciated that in other embodiments, threads 184 may be internal, or female, threads, and threads 186, 188 may be external, or male, threads.

Figure 16D:
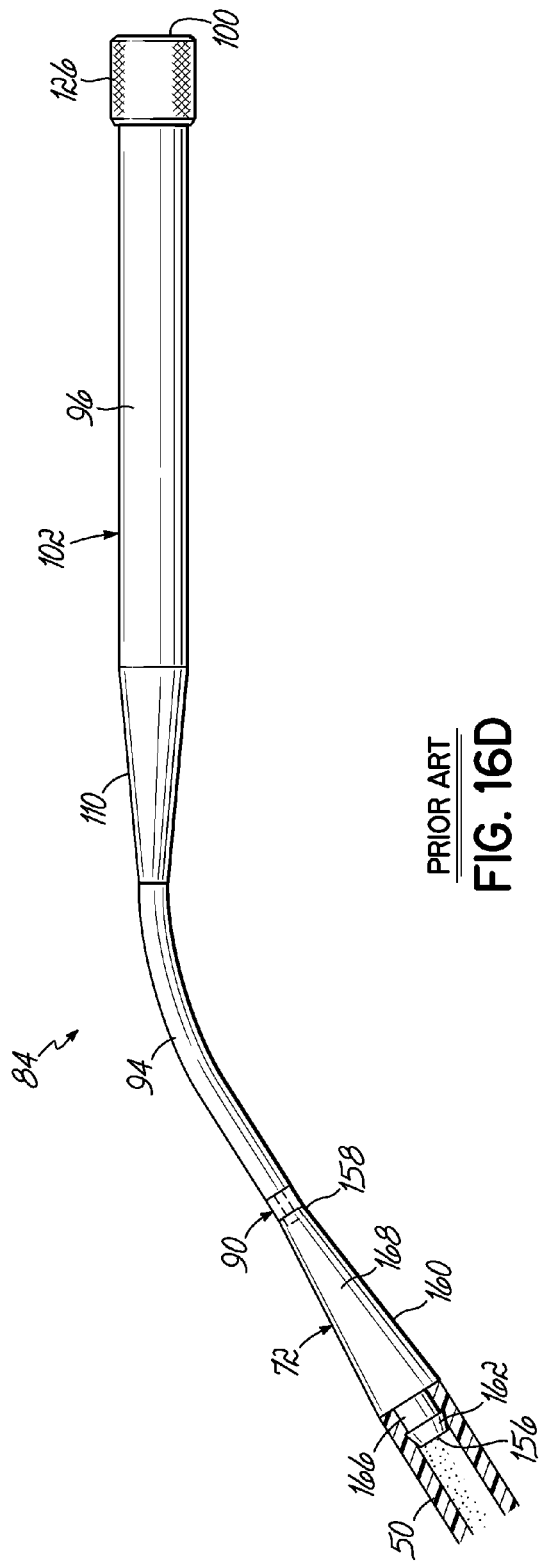

In one embodiment, the first connecting structure 90 may include a sleeve 194 that is defined in part by the threads 186 of the first connecting structure 90. The sleeve 194 may be independently rotatable of the cannula plug 72 to facilitate engagement of threads 186 with threads 184 without disturbing the cannula plug 72 or the cannula 50 (FIG. 16D). For example, the sleeve 194 may be positioned over and attached to a peg 196 that protrudes from the distal end 158 of the cannula plug 72, and the peg 196 may be affixed to an anchor 198 within the body 160 of the plug 72. In one embodiment, the distal end 158 may comprise a substantially constant cross section. In one embodiment the anchor 198 may be retained in the cannula plug 72 directly during a molding process used to form the plug 72. The anchor may comprise a larger cross section than the peg 196 in order to provide a more permanent hold. Furthermore, a screw 200 or other attachment means may be placed into the peg 196 in order to retain the sleeve 194. Alternatively, in another embodiment the sleeve 194 may be attached to the plug 72 by means of a rivet.

Figure 17A:
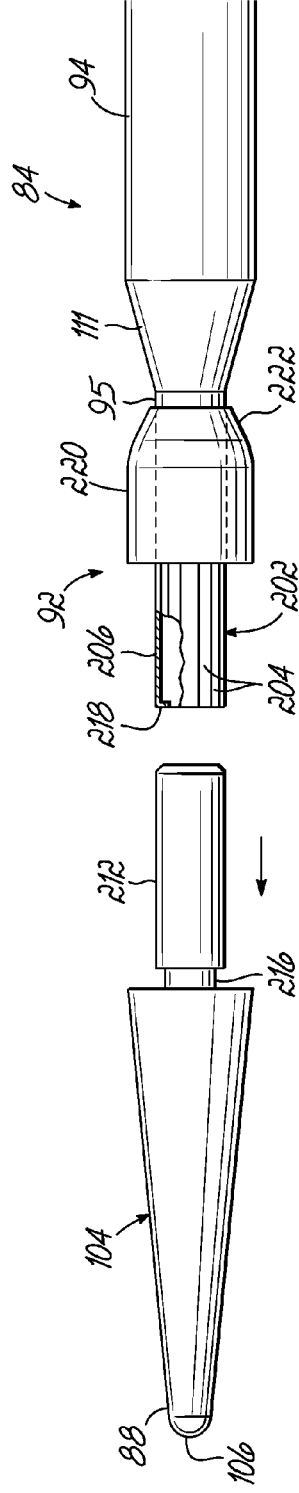
Figure 17B:
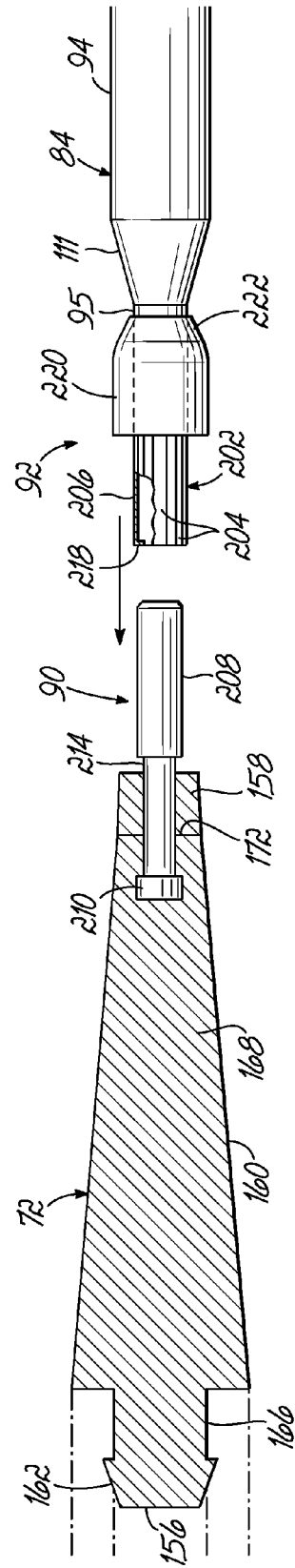

FIGS. 17A-17D show another embodiment of the system where the first and second connecting structures 90, 92 are configured to frictionally engage one another. More specifically, the second connecting structure 92 may be defined in part by a clip 202. For example, the clip 202 may include a sleeve or collet 204 having a plurality of expandable flanges or arms 206. In one embodiment, the flanges or arms 206 may be constructed of a metal material. Furthermore, the first connecting structure 90 may be defined in part by a pin 208 for frictionally engaging the clip 202. The pin 208 may protrude from the distal end 158 of the cannula plug 72. Furthermore, the pin 208 may be affixed to an anchor 210 within the body 160 of the plug 72. Moreover, the tunneling device 84 may include a detachable tip 104 having a pin 212 for frictionally engaging the clip 202. In this manner, a practitioner may direct the tunneling device 84 through a patient's intercostal space to a location proximate the cannula plug 72, as previously described. Once the distal end 88 of the tunneling device 84 is adjacent or near the first connecting structure 90, the practitioner may remove the detachable tip 104 by disengaging the pin 212 of the detachable tip 104 from the clip 202 of the second connecting structure 92, as shown in FIG. 17A. The practitioner may then provide a connection between the tunneling device 84 and the cannula plug 72 by engaging the pin 208 of the first connecting structure 90 with the clip 202 of the second connecting structure 92, as illustrated in FIGS. 17B and 17C. In one embodiment, at least a portion of the clip 202 may be tapered in order to provide a smooth transition as the tunneling device 84 is retracted through the intercostal space to a point where the cannula plug 72 traverses the intercostal space. To this end, the clip 202 may be fixed to an elongate dilator 95, which may be connected to the first elongate dilator 94 of the tunneling device 84 with a tapered section 111 provided therebetween.

In one embodiment, at least one of the pins 208, 212 may be tapered to provide a smooth expansion of the flanges 206 as a pin 208, 212 is inserted into the clip 202. In addition, the pins 208, 212 may include relief channels 214, 216. Furthermore, the clip 202 may include fingers 218 positioned on the flanges 206, and the fingers 218 may be engageable with the relief channels 214, 216 for securing a pin 208, 212 relative to the clip 202, as shown in FIG. 17C. In order to disengage the tunneling device 84 and cannula plug 72, the practitioner may need to pull the pin 208 away from the clip 202 such that the relief channel 214 may disengage from the fingers 218. The second connecting structure 92 may further include a retention sleeve 220 that may be slid over the clip 202 to secure the flanges 206 over a pin 208, 212, as illustrated in FIGS. 17C and 17D. For example, the retention sleeve 220 may move with tension so that it may not slide back and forth freely. Rather, a practitioner may be required to manually retract the retention sleeve 220 prior to disengaging the tunneling device 84 and cannula plug 72. In addition, the retention sleeve 220 may include a tapered section 222 in order to provide a smooth transition as the tunneling device 84 is retracted through the intercostal space to a point where the cannula plug 72 traverses the intercostal space.

While the figures may show the second connecting structures 92 associated with a certain embodiment of the tunneling device 84, the disclosure herein is not limited to such possibilities. It is anticipated that any of the second connecting structures 92 may be associated with any embodiment of the tunneling device 84. Moreover, multiple second connecting structures 92 may be included on the tunneling device 84 in order to provide versatility in the procedure. For example, the tunneling device 84 may include a second connecting structure 92, such as a hook 116, for accepting a loop 120, as well as a threaded portion (i.e., annular grooves 152) for engaging with the cavity of a cannula plug 72 as discussed above (FIGS. 12, 15 and 16). It is possible in alternative embodiments that the cannula plug 72 may include any of the second connecting structures 92 as described herein, while the tunneling device 84 may include any of the first connecting structures 90 as described herein. Moreover, the first and second connecting structures 90, 92 may engage in manners other than those described herein. For example, one or both of the first and second connecting structures 90, 92 may include magnetic features that allow magnetic coupling or engagement therebetween. More specifically, the first connecting structure 90 may comprise a first magnet (not shown), which may magnetically couple to a second magnet (not shown) that comprises the second connecting structure 92. Additionally, the cannula plug 72 and/or the tunneling device 84 may include features to complement the magnetic engagement, or that provide additional engagement force between the cannula plug and tunneling device, including features of the first and second connecting structures 90, 92 described herein.

Furthermore, the force provided between the first and second connecting structures 90, 92 must be configured to prevent the unwanted disconnection of the cannula 50 from the tunneling device 84 as the tunneling device 84 and cannula 50 are retracted through the thoracic cavity 76, further through the intercostal space, and into the pump pocket 78. As discussed herein, the tunneling device 84 and the cannula plug 72 may include features to reduce the forces that occur during retraction through tissue.

Figure 18C:
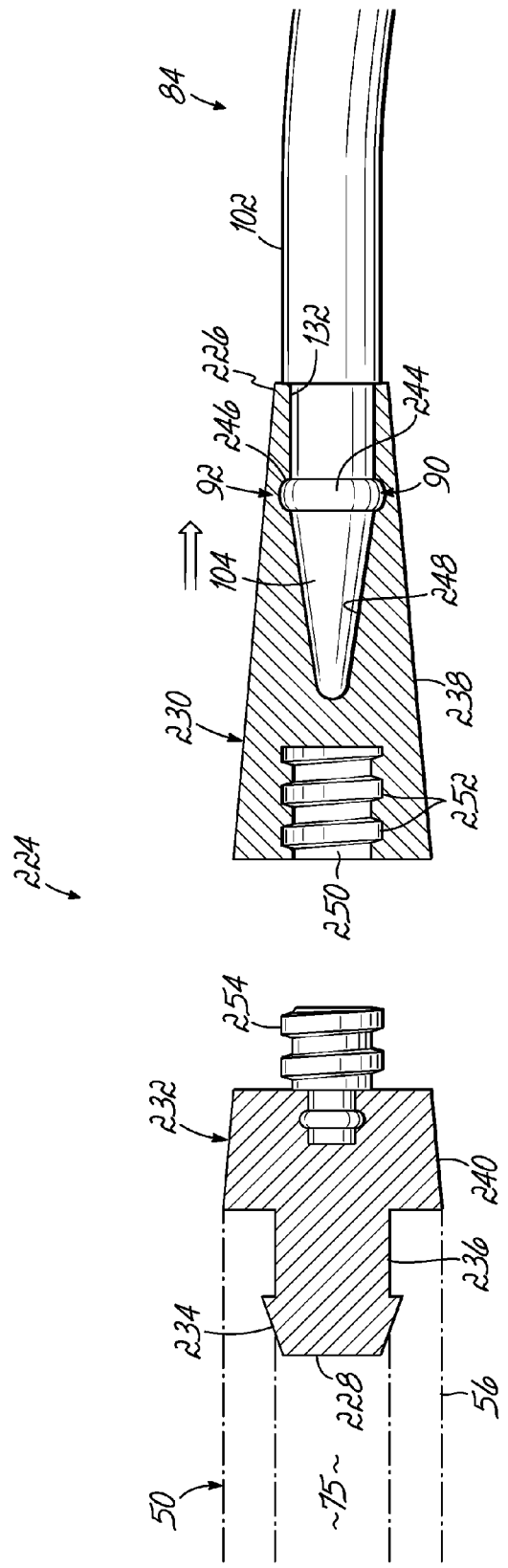

With reference to FIGS. 18A-C, a cannula plug 224 includes a proximal end 226, a distal end 228, and a body therebetween. The cannula plug 224 further includes a first plug part 230 and a second plug part 232 that are selectively engageable. Disengaging the first and second plug parts 230, 232 allows for in situ connection and disconnection of the first and second plug parts. At the distal end of the second plug part 232 is a stopper member 234. The stopper member 234 has a tapered, generally frustroconical shape that allows a practitioner to more easily insert the stopper member 234 into the lumen 75 of the cannula 50. In some embodiments, it may be provided that the stopper member 234 is configured to block flow of fluid from and seal the proximal end 56 of the cannula 50. The shape and configuration of the stopper member 234 as shown is but one embodiment, and it is appreciated that different shapes and configurations of the stopper member 234 that provide ease of insertion into the cannula 50 are possible. Preferably, the stopper member 234 engages the lumen 75 of the cannula 50 with an amount of interference and frictional force sufficient to prevent the unwanted removal of the cannula plug 224 from the cannula 50 during use. As discussed in more detail below, the cannula plug 224 includes features that may reduce the force required for traversing the cannula plug 224 through the intercostal tissue. These features therefore may reduce the likelihood of the unwanted removal of the cannula plug 224 from the cannula lumen 75. Extending proximally from the stopper member 234 is a generally cylindrical portion, or a neck 236, having a smaller outer diameter than the stopper member 234. The configuration of the neck 236 may provide an ease of removal benefit once the practitioner desires to remove the cannula plug 224 from the cannula 50.

Along the body of the plug 224, the first and second plug parts 230, 232 include elongate frustroconical members 238, 240, respectively. In FIG. 18A, the elongate frustroconical member 240 includes an aperture 242 near the distal end. As discussed herein, the aperture 242 may be provided as part of the second connecting structure 92 in order to selectively engage with the first connecting structure 90. As discussed above, once the first and second connecting structures 90, 92 are engaged, the cannula 50 and the tunneling device 84 are connected, and the cannula 50 may be directed adjacent the inlet of the pump 54 in the pump pocket 78.

As the tunneling device 84 is retracted to direct the cannula 50 to the pump pocket 78, the cannula plug 224 must also traverse the tissue interior to the pump pocket 78, such as an adjacent intercostal space. The elongate frustroconical members 238, 240 are configured to gently dilate, rather than tear or otherwise injure, the tissue as the cannula plug 224 traverses the intercostal space. Notably, the location of the tissue into which the tunneling device 84 is directed is the location where the cannula plug 224, and thus the cannula 50, may exit. In at least one of the embodiments of the system as described herein, the diameter of the largest portion of the elongate frustroconical members 238, 240 corresponds with, or is substantially equal to, the diameter of the second elongate dilator 96 of the tunneling device 84. Providing the cannula plug 224 with a largest diameter substantially equal to that of the tunneling device 84 (not including the handle 126) may reduce the force required to direct the cannula plug 224 through the intercostal tissue, as the tissue will already have been dilated by the tunneling device 84. This benefit reduces the likelihood of the unwanted removal of the cannula plug 224 from the proximal end of the cannula 50 and also reduces trauma to the patient 14. The cannula plug 224 may also be provided with a lubricious coating in order to reduce the frictional forces associated with traversing the tissue.

FIGS. 18A-C show an embodiment of the system where the first and second connecting structures 90, 92 are configured to frictionally engage one another. A first connecting structure 90 is on the tapered tip 104 of the tunneling device 84. In some embodiments, a portion of the first connecting structure 90 may be within the tapered tip 104 or proximal of the tapered tip 104. More specifically, the first connecting structure 90 shown in FIG. 18A is defined at least in part by an annular ring 244. The annular ring 244 is configured to engage with the second connecting structure 92. The second connecting structure 92 may be defined in part by an annular groove 246 inside a cavity 248 of the first plug part 230. At least a portion of the tunneling device 84 and the annular ring 244 is configured to be accepted into the cavity 248 of the cannula plug 224. The annular ring 244 may engage with the annular groove 246 to connect the first and second connecting structures 90, 92. More specifically, the cavity 248 of the cannula plug 224 is configured to receive and "grab," or frictionally secure the annular ring 244 of the tunneling device 84. The annular ring 244 may be molded into the first elongate dilator 94 as an integral component or, alternatively, may be a separately manufactured and added component.

The annular groove 246 may be made from an elastomeric material that is configured to allow the insertion of the tunneling device 84 into the cavity 248. The annular groove 246 is also configured to prevent the removal of the tunneling device 84 from the aperture 242 when the tunneling device 84 is retracted to direct the cannula 50 to the pump pocket 78. Such materials may include silicone, urethane, or other elastomeric materials. The first plug part 230 could be configured such that an inner portion including the cavity 248 is an elastomeric material while the outer portion is a different material. Alternatively, the entire cannula plug 224 could comprise the elastomeric material.

Furthermore, the force provided between the first and second connecting structures 90, 92 must be configured to prevent the unwanted disconnection of the cannula 50 from the tunneling device 84 as the tunneling device 84 and cannula 50 are retracted through the thoracic cavity 76, further through the intercostal space, and into the pump pocket 78. As discussed herein, the tunneling device 84 and the cannula plug 224 may include features to reduce the forces that occur during retraction through tissue.

FIGS. 18A-C also show an embodiment where the first and second plug parts 230, 232 are configured to threadably engage, or interlock, one another. More specifically, the first plug part 230 includes a cavity 250 having threads 252, and the second plug part 232 includes threads 254 (shown in FIG. 18C). The threads 252 are configured to mate with the threads 254 of the first plug part 230. The first and second plug parts 230, 232 may be initially engaged, as shown in FIGS. 18A and 18B. Once the proximal end 56 of the cannula 50 is adjacent or near the pump 54, the practitioner may disconnect the tunneling device 84 and the cannula plug 224. In order to disconnect the tunneling device 84 and the cannula plug 224, the practitioner may disengage the threads 254 of the first plug part 230 from the threads 252 of the second plug part 232, as shown in FIG. 18C. In the embodiment shown, threads 254 are an internal, or female, luer lock fitting, while threads 252 are an external, or male, luer lock fitting. However, it should be appreciated that in other embodiments, threads 252 may be an internal, or female, lock fitting, and threads 254 may be an external, or male, lock fitting.

Figure 19A:
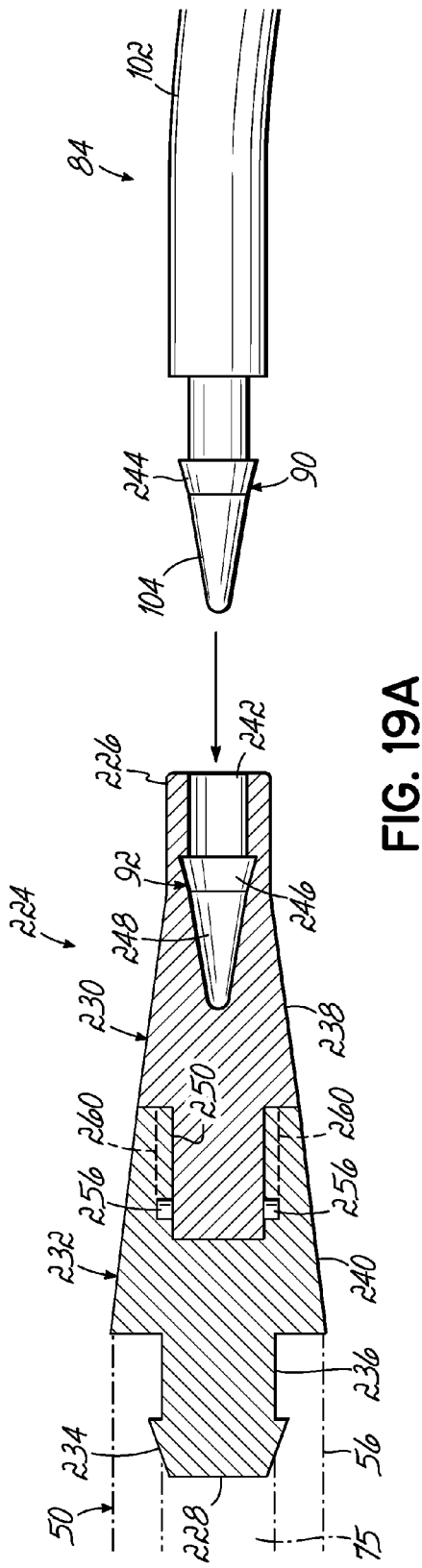
Figure 19B:
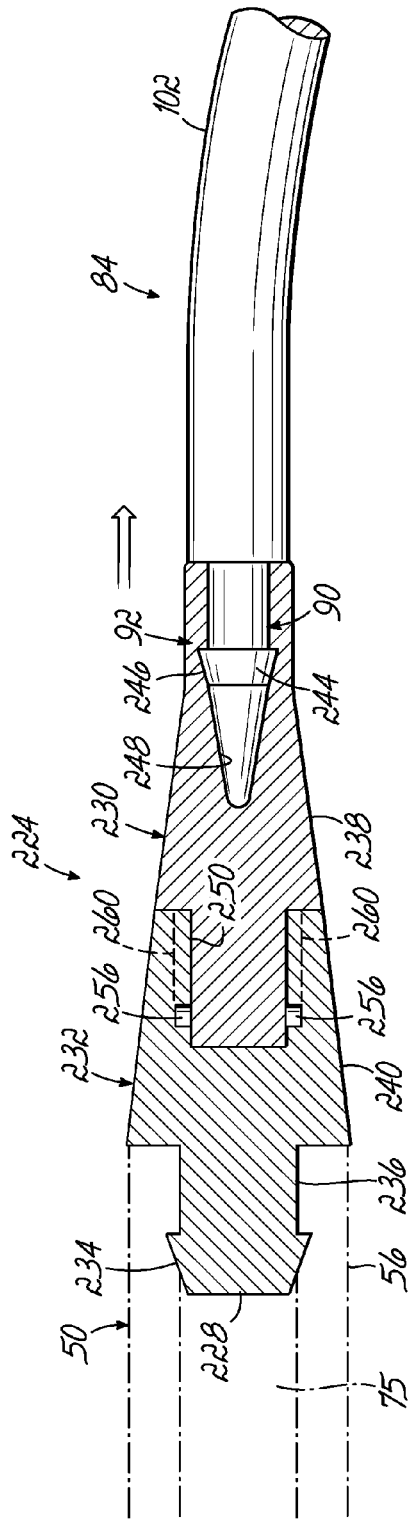

FIGS. 19A-C show another embodiment of the system where the first and second plug parts 230, 232 are configured to frictionally engage one another. With specific reference to FIG. 19C, locking pins 256 are adjacent the distal end of the first plug part 230. The locking pins 256 are configured to be accepted into L-shaped slots 258 in the cavity 250 of the second plug part 232. The L-shaped slots 258 have first portions 260 and second, lateral portions 262 at the end of the first portions 260 opposite the aperture 242 of the second plug part 232. In order to prevent relative movement between the first and second plug parts 230, 232, the locking pins 256 must be directed into the first portions 260 of L-shaped slots 258 and rotated into and in engagement with the second, lateral portions 262. The first and second plug parts 230, 232 may be initially engaged, as shown in FIGS. 19A and 19B. Once the proximal end 56 of the cannula 50 is adjacent or near the pump 54, the practitioner may disconnect the tunneling device 84 and the cannula plug 224. In order to disconnect the tunneling device 84 and the cannula plug 224, the practitioner may rotate the first plug part 230, where the locking pins 256 are no longer engaged with the second, lateral portions 262 of the L-shaped slots 258. The practitioner may then withdraw the first plug part 230 from the cavity 250 of the second plug part 232.

Furthermore, the force provided in the engagement of the first and second plug parts 230, 232 must be configured to prevent the unwanted disconnection of the first and second plug parts 230, 232 as the tunneling device 84 and cannula 50 are retracted through the thoracic cavity 76, further through the intercostal space, and into the pump pocket 78.

As shown in FIG. 20, grips 264 may be provided on one or both of the first and second plug parts 230, 232 to allow for easy manipulation by the practitioner. The embodiments of the cannula plug 224 as shown in FIGS. 18-20 and as described in this disclosure are meant to be illustrative. It is anticipated that alternative designs of the cannula plug 224 are possible.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A system for facilitating fluid connection between a blood pump and a circulatory system of a patient, comprising:
   a cannula having proximal and distal ends, the distal end of the cannula adapted to be in fluid communication with the circulatory system and the proximal end of the cannula configured to couple to an inlet of the blood pump;
   a tunneling device configured to be inserted into a body of a patient to direct the proximal end of the cannula adjacent to the inlet for connection thereto, the tunneling device having a first connecting structure; and
   a plug having a first plug part and a second plug part, the first plug part having a second connecting structure and the second plug part configured to be inserted in the proximal end of the cannula,
   wherein the first and second connecting structures are selectively engageable to allow in situ connection between the cannula and tunneling device, and
   wherein the first and second plug parts are selectively disengageable to allow in situ disconnection between the cannula and the tunneling device when the proximal end of the cannula is adjacent to the inlet.

2. The system of claim 1, wherein:
   the first connecting structure comprises a groove on a distal end of the tunneling device; and
   the second connecting structure comprises:
      a cavity in the first plug part for receiving the distal end of the tunneling device; and
      a rib in the cavity, the rib engageable with the groove for securing the first connecting structure relative to the second connecting structure.

3. The system of claim 1, wherein:
   the first plug part includes a cavity for receiving a distal portion of the second plug part, the cavity having threads; and
   the second plug part includes threads for mating with the threads of the first plug part for securing the second plug part relative to the first plug part.

4. The system of claim 1, wherein:
   the first plug part includes a cavity for receiving a distal portion of the second plug part, the cavity having at least one slot; and
   the second plug part includes at least one locking pin, the at least one locking pin engageable with the at least one slot for securing the second plug part relative to the first plug part.

5. The system of claim 1, wherein the second plug part is distal of the first plug part.

6. The system of claim 1, wherein a distal end of the first plug part and a proximal end of the second plug part have substantially equal diameters.

7. A method of facilitating fluid connection between a blood pump and a circulatory system of a patient using a system, the system comprising a cannula having proximal and distal ends, a tunneling device having a first connecting structure, and a plug having a first plug part having a second connecting structure and a second plug part, the method comprising:
   directing the distal end of the cannula into fluid communication with the circulatory system;
   inserting the blood pump into a body of the patient;
   inserting the tunneling device into the body of the patient;
   selectively engaging the first connecting structure of the tunneling device with the second connecting structure of the first plug part, the first and second plug parts being engaged and the second plug part being engaged with the proximal end of the cannula;
   using the tunneling device to direct the proximal end of the cannula adjacent to an inlet of the blood pump;
   selectively disengaging the first plug part from the second plug part;
   selectively disengaging the second plug part from the proximal end of the cannula; and
   connecting the proximal end of the cannula to the inlet.

8. The method of claim 7, wherein selectively engaging the first connecting structure with the second connecting structure includes engaging a rib on a distal end of the tunneling device with a cavity in the first plug part.

9. The method of claim 7, wherein selectively disengaging the first plug part from the second plug part includes disengaging threads on the second plug part from threads in a cavity of the first plug part.

10. The method of claim 7, wherein selectively disengaging the first plug part from the second plug part includes disengaging at least one pin on the second plug part from at least one slot on the first plug part.

* * * * *